(12) United States Patent
Neumann

(10) Patent No.: US 10,593,431 B1
(45) Date of Patent: Mar. 17, 2020

(54) METHODS AND SYSTEMS FOR CAUSATIVE CHAINING OF PROGNOSTIC LABEL CLASSIFICATIONS

(71) Applicant: Kenneth Neumann, Lakewood, CO (US)

(72) Inventor: Kenneth Neumann, Lakewood, CO (US)

(73) Assignee: KPN Innovations, LLC, Lakewood, CO (US)

( * ) Notice: Subject to any disclaimer, the term of this patent is extended or adjusted under 35 U.S.C. 154(b) by 0 days.

(21) Appl. No.: 16/430,387

(22) Filed: Jun. 3, 2019

(51) Int. Cl.
*G16H 50/70* (2018.01)
*G16B 40/00* (2019.01)
*G06N 20/10* (2019.01)
*G06N 7/00* (2006.01)
*G06K 9/62* (2006.01)

(52) U.S. Cl.
CPC .......... *G16H 50/70* (2018.01); *G06K 9/6259* (2013.01); *G06N 7/005* (2013.01); *G06N 20/10* (2019.01); *G16B 40/00* (2019.02)

(58) Field of Classification Search
None
See application file for complete search history.

(56) References Cited

U.S. PATENT DOCUMENTS

| | | | |
|---|---|---|---|
| 7,433,853 B2* | 10/2008 | Brockway | A61B 5/0002 706/45 |
| 9,375,142 B2* | 6/2016 | Schultz | A61B 5/0002 |
| 9,532,721 B2 | 1/2017 | Batchinsky et al. | |
| 9,764,136 B2 | 9/2017 | McIntyre et al. | |
| 9,916,538 B2* | 3/2018 | Zadeh | G06N 7/005 |
| 2004/0103001 A1 | 5/2004 | Mazar | |

(Continued)

FOREIGN PATENT DOCUMENTS

| CN | 108198620 A | 6/2018 |
|---|---|---|
| CN | 109346169 A | 2/2019 |
| WO | 2001026026 | 4/2001 |

OTHER PUBLICATIONS

Jiang et al., Jun. 22, 2017, Artificial intelligence in healthcare: past, present and future; https://svn.bmj.com/content/2/4/230.

(Continued)

*Primary Examiner* — Michael Tomaszewski
*Assistant Examiner* — Jay M. Patel
(74) *Attorney, Agent, or Firm* — Caldwell Intellectual Property

(57) ABSTRACT

A system for causative chaining of prognostic label classifications includes a classification device configured to receive training data including a plurality of first data entries, each including at least a first element of physiological state data and at least a correlated first prognostic label and a plurality of second data entries, each including at least a second prognostic label and at least a correlated third prognostic label, and to record at least a first biological extraction. The system includes a prognostic label learner configured to generate at least a first prognostic output as a function of the first training set and the at least a physiological test sample, and a causal link learner configured to generate at least a second prognostic output causally linked to the first prognostic output as a function of the second training set and the at least a first prognostic output.

12 Claims, 10 Drawing Sheets

(56) References Cited

U.S. PATENT DOCUMENTS

| | | | |
|---|---|---|---|
| 2005/0209785 A1* | 9/2005 | Wells | G16H 50/20 702/19 |
| 2006/0287969 A1* | 12/2006 | Li | G16B 40/00 706/16 |
| 2008/0033899 A1* | 2/2008 | Barnhill | G06K 9/6228 706/48 |
| 2008/0103403 A1* | 5/2008 | Cohen | G16H 50/20 600/509 |
| 2009/0030290 A1 | 1/2009 | Kozuch | |
| 2010/0205124 A1* | 8/2010 | Ben-Hur | G06K 9/6215 706/12 |
| 2010/0256988 A1* | 10/2010 | Barnhill | G06K 9/6228 705/2 |
| 2012/0136629 A1* | 5/2012 | Tamaki | G05B 23/0254 702/183 |
| 2014/0201126 A1* | 7/2014 | Zadeh | A61B 5/4803 706/52 |
| 2015/0220838 A1* | 8/2015 | Martin | G06N 5/04 706/12 |
| 2016/0235372 A1 | 8/2016 | Schneider et al. | |
| 2017/0091937 A1* | 3/2017 | Barnes | C12Q 1/6886 |
| 2017/0175169 A1* | 6/2017 | Lee | G01N 33/54373 |
| 2018/0000428 A1* | 1/2018 | Swiston | G16H 50/30 |
| 2018/0315489 A1 | 11/2018 | Jaruzel, II et al. | |
| 2018/0330059 A1 | 11/2018 | Bates et al. | |
| 2019/0026655 A1 | 1/2019 | Xie et al. | |
| 2019/0038202 A1* | 2/2019 | Wall | G16H 10/20 |
| 2019/0110754 A1 | 4/2019 | Rao et al. | |

OTHER PUBLICATIONS

Banaee et al.; Data Mining for Wearable Sensors in Health Monitoring Systems: A Review of Recent Trends and Challenges; https://www.ncbi.nlm.nih.gov/pmc/articles/PMC3892855/.

* cited by examiner

METHODS AND SYSTEMS FOR CAUSATIVE CHAINING OF PROGNOSTIC LABEL CLASSIFICATIONS

FIELD OF THE INVENTION

The present invention generally relates to the field of machine learning. In particular, the present invention is directed to methods and systems for causative chaining of prognostic label classifications.

BACKGROUND

Automated analysis of physiological data can be highly challenging due to the multiplicity of types and sources of data to be analyzed, which in turn is a reflection of the immense complexity of systems so represented. Burgeoning knowledge concerning microscopic and macroscopic physiological states, and concomitantly expanding modes of detection and analysis of the same, have further exacerbated this problem.

SUMMARY OF THE DISCLOSURE

In an aspect, a system for causative chaining of prognostic label classifications includes a classification device, the classification device designed and configured to receive training data, where receiving the training data further includes receiving a first training set including a plurality of first data entries, each first data entry of the plurality of first data entries including at least a first element of physiological state data and at least a correlated first prognostic label and receiving a second training set including a plurality of second data entries, each second data entry of the plurality of second data entries including at least a second prognostic label and at least a correlated third prognostic label. The classification device is designed and configured to record at least a first biological extraction. The system includes a prognostic label learner operating on the classification device, the prognostic label learner designed and configured to generate at least a first prognostic output as a function of the first training set and the at least a physiological test sample. The system includes a causal link learner operating on the classification device, the causal link learner designed and configured to generate the at least a second prognostic output as a function of the second training set and the at least a first prognostic output, wherein the at least a second prognostic output represents a cause of the at least a first prognostic output.

In another aspect, a method of causative chaining of prognostic label classifications includes receiving, by a classification device, training data, where receiving the training data further includes receiving a first training set including a plurality of first data entries, each first data entry of the plurality of first data entries including at least a first element of physiological state data and at least a correlated first prognostic label, and receiving a second training set including a plurality of second data entries, each second data entry of the plurality of second data entries including at least a second prognostic label and at least a correlated third prognostic label. The method includes recording, by the classification device, at least a first biological extraction. The method includes generating, by the classification device, at least a first prognostic output as a function of the first training set and the at least a physiological test sample. The method includes generating, by the classification device, at least a second prognostic output as a function of the second training set and the at least a first prognostic output, wherein the at least a second prognostic output represents a cause of the at least a first prognostic output.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

Embodiments of systems and methods disclosed herein may classify physiological samples to one or more prognostic labels using training sets correlating physiological state data to prognostic labels; prognostic labels are further linked to causally related prognostic labels via additional machine-learning processes. Categorization of data elements in training sets may be accomplished using unsupervised clustering algorithms; categorization may alternatively or additionally involve expert data inputs provided by graphical user interface entries or extracted using language processing algorithms from a corpus of subject-specific documents.

Figure 1:
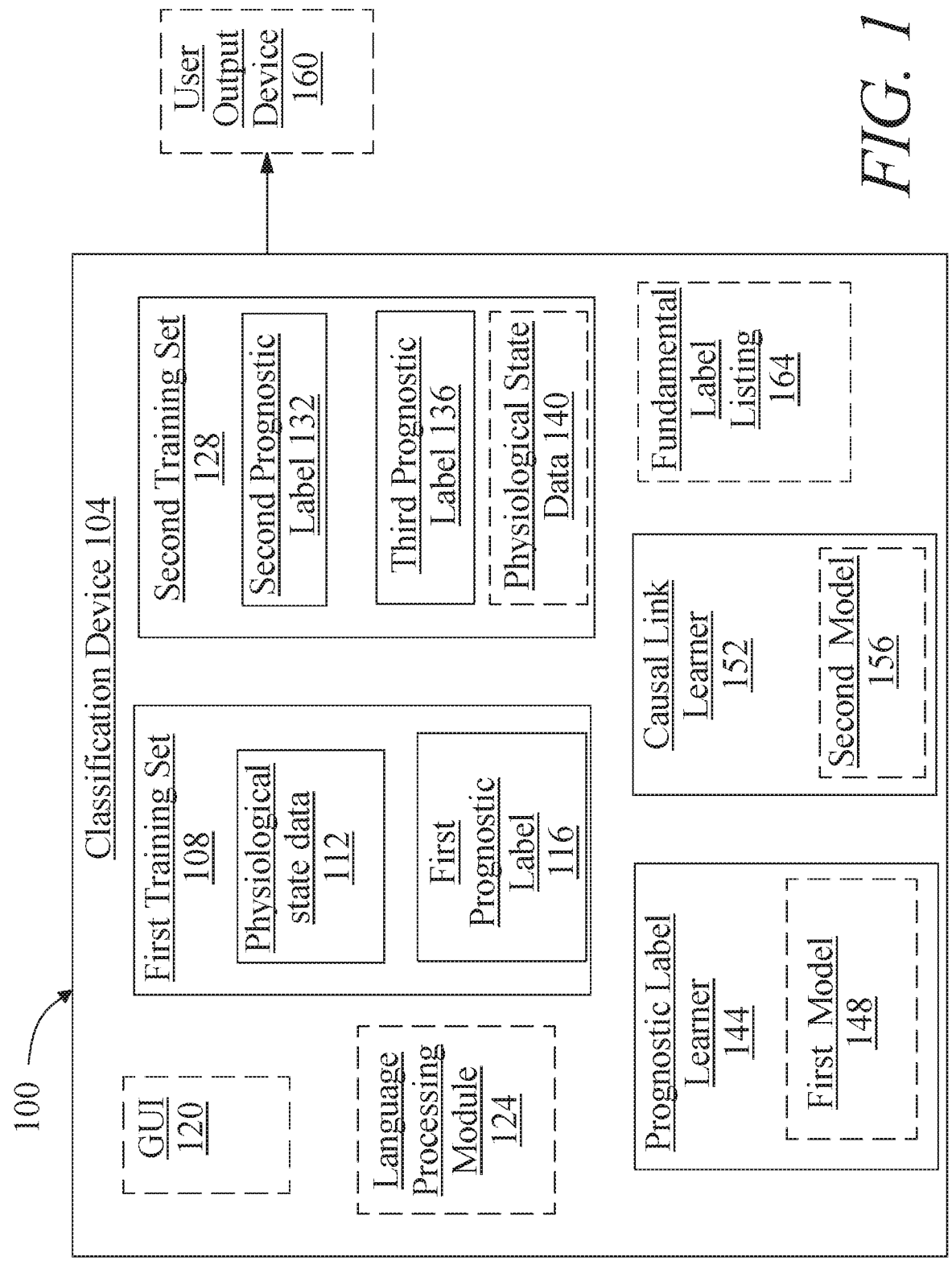
FIG. 1 is a block diagram illustrating an exemplary embodiment of a system for causative chaining of prognostic label classifications.

Referring now to FIG. 1, an exemplary embodiment of a system 100 for causative chaining of prognostic label classifications is illustrated. System includes a classification device 104. Classification device 104 may include any computing device as described in this disclosure, including without limitation a microcontroller, microprocessor, digital signal processor (DSP) and/or system on a chip (SoC) as described in this disclosure. Classification device 104 may be housed with, may be incorporated in, or may incorporate one or more sensors of at least a sensor. Computing device may include, be included in, and/or communicate with a mobile device such as a mobile telephone or smartphone. Classification device 104 may include a single computing device operating independently, or may include two or more computing device operating in concert, in parallel, sequentially or the like; two or more computing devices may be included together in a single computing device or in two or more computing devices. Classification device 104 with one or more additional devices as described below in further detail via a network interface device. Network interface device may be utilized for connecting a classification device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Classification device 104 may include but is not limited to, for example, a classification device 104 or cluster of computing devices in a first location and a second computing device or cluster of computing devices in a second location. Classification device 104 may include one or more computing devices dedicated to data storage, security, distribution of traffic for load balancing, and the like. Classification device 104 may distribute one or more computing tasks as described below across a plurality of computing devices of computing device, which may operate in parallel, in series, redundantly, or in any other manner used for distribution of tasks or memory between computing devices. Classification device 104 may be implemented using a "shared nothing" architecture in which data is cached at the worker, in an embodiment, this may enable scalability of system 100 and/or computing device.

Still referring to FIG. 1, classification device 104 and/or one or more modules operating thereon may be designed and/or configured to perform any method, method step, or sequence of method steps in any embodiment described in this disclosure, in any order and with any degree of repetition. For instance, classification device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Classification device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Continuing to refer to FIG. 1, classification device 104 may be designed and configured to receive training data. Training data, as used herein, is data containing correlation that a machine-learning process may use to model relationships between two or more categories of data elements. For instance, and without limitation, training data may include a plurality of data entries, each entry representing a set of data elements that were recorded, received, and/or generated together; data elements may be correlated by shared existence in a given data entry, by proximity in a given data entry, or the like. Multiple data entries in training data may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data according to various correlations; correlations may indicate causative and/or predictive links between categories of data elements, which may be modeled as relationships such as mathematical relationships by machine-learning processes as described in further detail below. Training data may be formatted and/or organized by categories of data elements, for instance by associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements; for instance, and without limitation, training data may be provided in fixed-length formats, formats linking positions of data to categories such as comma-separated value (CSV) formats and/or self-describing formats such as extensible markup language (XML), enabling processes or devices to detect categories of data.

Alternatively or additionally, and still referring to FIG. 1, training data may include one or more elements that are not categorized; that is, training data may not be formatted or contain descriptors for some elements of data. Machine-learning algorithms and/or other processes may sort training data according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name and/or a description of a medical condition or therapy may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data to be made applicable for two or more distinct machine-learning algorithms as described in further detail below.

Still referring to FIG. 1, categorization device may be configured to receive a first training set 108 including a plurality of first data entries, each first data entry of the first training set 108 including at least an element of physiological state data and at least a correlated first prognostic label 116. At least an element of physiological state data may include any data indicative of a person's physiological state; physiological state may be evaluated with regard to one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. Physiological state data may include, without limitation, hematological data, such as red blood cell count, which may include a total number of red blood cells in a person's blood and/or in a blood sample, hemoglobin levels, hematocrit representing a percentage of blood in a person and/or sample that is composed of red blood cells, mean corpuscular volume, which may be an estimate of the average red blood cell size, mean corpuscular hemoglobin, which may measure average weight of hemoglobin per red blood cell, mean corpuscular hemoglobin concentration, which may measure an average concentration of hemoglobin in red blood cells, platelet count, mean platelet volume which may measure the average size of platelets, red blood cell distribution width, which measures variation in red blood cell size, absolute neutrophils, which measures the number of neutrophil white blood cells, absolute quantities of lymphocytes such as B-cells, T-cells, Natural Killer Cells, and the like, absolute numbers of monocytes including macrophage precursors, absolute numbers of eosinophils, and/or absolute counts of basophils. Physiological state data may include, without limitation, immune function data such as Interleukine-6 (IL-6), TNF-alpha, systemic inflammatory cytokines, and the like.

Continuing to refer to FIG. 1, physiological state data may include, without limitation, data describing blood-born lipids, including total cholesterol levels, high-density lipoprotein (HDL) cholesterol levels, low-density lipoprotein (LDL) cholesterol levels, very low-density lipoprotein (VLDL) cholesterol levels, levels of triglycerides, and/or any other quantity of any blood-born lipid or lipid-containing substance. Physiological state data may include measures of glucose metabolism such as fasting glucose levels and/or hemoglobin Al-C (HbA1c) levels. Physiological state data may include, without limitation, one or more measures associated with endocrine function, such as without limitation, quantities of dehydroepiandrosterone (DHEAS), DHEA-Sulfate, quantities of cortisol, ratio of DHEAS to cortisol, quantities of testosterone quantities of estrogen, quantities of growth hormone (GH), insulin-like growth factor 1 (IGF-1), quantities of adipokines such as adiponectin, leptin, and/or ghrelin, quantities of somatostatin, progesterone, or the like. Physiological state data may include measures of estimated glomerular filtration rate (eGFR). Physiological state data may include quantities of C-reactive protein, estradiol, ferritin, folate, homocysteine, prostate-specific Ag, thyroid-stimulating hormone, vitamin D, 25 hydroxy, blood urea nitrogen, creatinine, sodium, potassium, chloride, carbon dioxide, uric acid, albumin, globulin, calcium, phosphorus, alkaline photophatase, alanine amino transferase, aspartate amino transferase, lactate dehydrogenase (LDH), bilirubin, gamma-glutamyl transferase (GGT), iron, and/or total iron binding capacity (TIBC), or the like. Physiological state data may include antinuclear antibody levels. Physiological state data may include aluminum levels. Physiological state data may include arsenic levels. Physiological state data may include levels of fibronigen, plasma cystatin C, and/or brain natriuretic peptide.

Continuing to refer to FIG. 1, physiological state data may include measures of lung function such as forced expiratory volume, one second (FEV-1) which measures how much air can be exhaled in one second following a deep inhalation, forced vital capacity (FVC), which measures the volume of air that may be contained in the lungs. Physiological state data may include a measurement blood pressure, including without limitation systolic and diastolic blood pressure. Physiological state data may include a measure of waist circumference. Physiological state data may include body mass index (BMI). Physiological state data may include one or more measures of bone mass and/or density such as dual-energy x-ray absorptiometry. Physiological state data may include one or more measures of muscle mass. Physiological state data may include one or more measures of physical capability such as without limitation measures of grip strength, evaluations of standing balance, evaluations of gait speed, pegboard tests, timed up and go tests, and/or chair rising tests.

Still viewing FIG. 1, physiological state data may include one or more measures of cognitive function, including without limitation Rey auditory verbal learning test results, California verbal learning test results, NIH toolbox picture sequence memory test, Digital symbol coding evaluations, and/or Verbal fluency evaluations. Physiological state data may include one or more evaluations of sensory ability, including measures of audition, vision, olfaction, gustation, vestibular function and pain.

Continuing to refer to FIG. 1, physiological state data may include psychological data. Psychological data may include any data generated using psychological, neuro-psychological, and/or cognitive evaluations, as well as diagnostic screening tests, personality tests, personal compatibility tests, or the like; such data may include, without limitation, numerical score data entered by an evaluating professional and/or by a subject performing a self-test such as a computerized questionnaire. Psychological data may include textual, video, or image data describing testing, analysis, and/or conclusions entered by a medical professional such as without limitation a psychologist, psychiatrist, psychotherapist, social worker, a medical doctor, or the like. Psychological data may include data gathered from user interactions with persons, documents, and/or computing devices; for instance, user patterns of purchases, including electronic purchases, communication such as via chat-rooms or the like, any textual, image, video, and/or data produced by the subject, any textual image, video and/or other data depicting and/or describing the subject, or the like. Any psychological data and/or data used to generate psychological data may be analyzed using machine-learning and/or language processing modules as described in this disclosure.

Still referring to FIG. 1, physiological state data may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Physiological state data may include proteomic data, which as used herein is data describing all proteins produced and/or modified by an organism, colony of organisms, or system of organisms, and/or a subset thereof. Physiological state data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below.

With continuing reference to FIG. 1, physiological state data may include one or more user-entered descriptions of a person's physiological state. One or more user-entered descriptions may include, without limitation, user descriptions of symptoms, which may include without limitation current or past physical, psychological, perceptual, and/or neurological symptoms, user descriptions of current or past physical, emotional, and/or psychological problems and/or concerns, user descriptions of past or current treatments, including therapies, nutritional regimens, exercise regimens, pharmaceuticals or the like, or any other user-entered data that a user may provide to a medical professional when seeking treatment and/or evaluation, and/or in response to medical intake papers, questionnaires, questions from medical professionals, or the like. Physiological state data may include any physiological state data, as described above, describing any multicellular organism living in or on a person including any parasitic and/or symbiotic organisms living in or on the persons; non-limiting examples may include mites, nematodes, flatworms, or the like. Examples of physiological state data described in this disclosure are presented for illustrative purposes only and are not meant to be exhaustive. Persons skilled in the art, upon reviewing the entirety of this disclosure, will be aware of various additional examples of physiological state data that may be used consistently with descriptions of systems and methods as provided in this disclosure.

Continuing to refer to FIG. 1, each element of first training set 108 includes at least a first prognostic label 116. A prognostic label, as described herein, is an element of data identifying and/or describing a current, incipient, or probable future medical condition affecting a person; medical condition may include a particular disease, one or more symptoms associated with a syndrome, a syndrome, and/or any other measure of current or future health and/or healthy aging. At least a prognostic label may be associated with a physical and/or somatic condition, a mental condition such as a mental illness, neurosis, or the like, or any other condition affecting human health that may be associated with one or more elements of physiological state data as described in further detail below. Conditions associated with prognostic labels may include, without limitation one or more diseases, defined for purposes herein as conditions that negatively affect structure and/or function of part or all of an organism. Conditions associated with prognostic labels may include, without limitation, acute or chronic infections, including without limitation infections by bacteria, archaea, viruses, viroids, prions, single-celled eukaryotic organisms such as amoeba, paramecia, trypanosomes, plasmodia, leishmania, and/or fungi, and/or multicellular parasites such as nematodes, arthropods, fungi, or the like. Prognostic labels may be associated with one or more immune disorders, including without limitation immunodeficiencies and/or auto-immune conditions. Prognostic labels may be associated with one or more metabolic disorders. Prognostic labels may be associated with one or more endocrine disorders. Prognostic labels may be associated with one or more cardiovascular disorders. Prognostic labels may be associated with one or more respiratory disorders. Prognostic labels may be associated with one or more disorders affecting connective tissue. Prognostic labels may be associated with one or more digestive disorders. Prognostic labels may be associated with one or more neurological disorders such as neuromuscular disorders, dementia, or the like. Prognostic labels may be associated with one or more disorders of the excretory system, including without limitation nephrological disorders. Prognostic labels may be associated with one or more liver disorders. Prognostic labels may be associated with one or more disorders of the bones such as osteoporosis. Prognostic labels may be associated with one or more disorders affecting joints, such as osteoarthritis, gout, and/or rheumatoid arthritis. Prognostic labels be associated with one or more cancers, including without limitation carcinomas, lymphomas, leukemias, germ cell tumor cancers, blastomas, and/or sarcomas. Prognostic labels may include descriptors of latent, dormant, and/or apparent disorders, diseases, and/or conditions. Prognostic labels may include descriptors of conditions for which a person may have a higher than average probability of development, such as a condition for which a person may have a "risk factor"; for instance, a person currently suffering from abdominal obesity may have a higher than average probability of developing type II diabetes. Prognostic labels may include descriptors of current, incipient, past, and/or potential future psychological and/or neurological conditions. The above-described examples are presented for illustrative purposes only and are not intended to be exhaustive. Persons skilled in the art, upon reviewing the entirety of this disclosure, will be aware of various additional examples of conditions that may be associated with prognostic labels as described in this disclosure.

Still referring to FIG. 1, at least a prognostic label may be stored in any suitable data and/or data type. For instance, and without limitation, at least a prognostic label may include textual data, such as numerical, character, and/or string data. Textual data may include a standardized name and/or code for a disease, disorder, or the like; codes may include diagnostic codes and/or diagnosis codes, which may include without limitation codes used in diagnosis classification systems such as without limitation the International Statistical Classification of Diseases and Related Health Problems (ICD), the Diagnostic and Statistical Manual of Mental Disorders (DSM 5), or the like. In general, there is no limitation on forms textual data or non-textual data used as at least a prognostic label may take; persons skilled in the art, upon reviewing the entirety of this disclosure, will be aware of various forms which may be suitable for use as at least a prognostic label consistently with this disclosure.

With continued reference to FIG. 1, in each first data element of first training set 108, at least a first prognostic label 116 of the data element is correlated with at least an element of physiological state data of the data element. In an embodiment, a first element of physiological state data 112 is correlated with at least a first prognostic label 116 where the first element of physiological state data 112 is located in the same data element and/or portion of data element as the at least a first prognostic label 116; for example, and without limitation, a first element of physiological state data 112 is correlated with a prognostic element where both first element of physiological state data 112 and prognostic element are contained within the same first data element of the first training set 108. As a further example, a first element of physiological state data 112 is correlated with a prognostic element where both share a category label as described in further detail below, where each is within a certain distance of the other within an ordered collection of data in data element, or the like. Still further, a first element of physiological state data 112 may be correlated with at least a first prognostic label 116 where the first element of physiological state data 112 and the at least a first prognostic label 116 share an origin, such as being data that was collected with regard to a single person or the like. In an embodiment, a first datum may be more closely correlated with a second datum in the same data element than with a third datum contained in the same data element; for instance, the first element and the second element may be closer to each other in an ordered set of data than either is to the third element, the first element and second element may be contained in the same subdivision and/or section of data while the third element is in a different subdivision and/or section of data, or the like. Persons skilled in the art, upon reviewing the entirety of this disclosure, will be aware of various forms and/or degrees of correlation between physiological data and prognostic labels that may exist in first training set 108 and/or first data element consistently with this disclosure.

In an embodiment, and still referring to FIG. 1, classification device 104 may be designed and configured to associate at least an element of physiological state data with at least a category from a list of significant categories of physiological state data. Significant categories of physiological state data may include labels and/or descriptors describing types of physiological state data that are identified as being of high relevance in identifying prognostic labels. As a non-limiting example, one or more categories may identify significant categories of physiological state data based on degree of diagnostic relevance to one or more impactful conditions and/or within one or more medical or public health fields. For instance, and without limitation, a particular set of biomarkers, test results, and/or biochemical information may be recognized in a given medical field as useful for identifying various disease conditions or prognoses within a relevant field. As a non-limiting example, and without limitation, physiological data describing red blood cells, such as red blood cell count, hemoglobin levels, hematocrit, mean corpuscular volume, mean corpuscular hemoglobin, and/or mean corpuscular hemoglobin concentration may be recognized as useful for identifying various conditions such as dehydration, high testosterone, nutrient deficiencies, kidney dysfunction, chronic inflammation, anemia, and/or blood loss. As an additional example, hemoglobin levels may be useful for identifying elevated testosterone, poor oxygen deliverability, thiamin deficiency, insulin resistance, anemia, liver disease, hypothyroidism, arginine deficiency, protein deficiency, inflammation, and/or nutrient deficiencies. In a further non-limiting example, hematocrit may be useful for identifying dehydration, elevated testosterone, poor oxygen deliverability, thiamin deficiency, insulin resistance, anemia, liver disease, hypothyroidism, arginine deficiency, protein deficiency, inflammation, and/or nutrient deficiencies. Similarly, measures of lipid levels in blood, such as total cholesterol, HDL, LDL, VLDL, triglycerides, LDL-C and/or HDL-C may be recognized as useful in identifying conditions such as poor thyroid function, insulin resistance, blood glucose dysregulation, magnesium deficiency, dehydration, kidney disease, familial hypercholesterolemia, liver dysfunction, oxidative stress, inflammation, malabsorption, anemia, alcohol abuse, diabetes, hypercholesterolemia, coronary artery disease, atherosclerosis, or the like. Persons skilled in the art, upon reviewing the entirety of this disclosure, will be aware of various additional categories of physiological data that may be used consistently with this disclosure.

Still referring to FIG. 1, classification device 104 may receive the list of significant categories according to any suitable process; for instance, and without limitation, classification device 104 may receive the list of significant categories from at least an expert. In an embodiment, classification device 104 and/or a user device connected to classification device 104 may provide a graphical user interface 120, which may include without limitation a form or other graphical element having data entry fields, wherein one or more experts, including without limitation clinical and/or scientific experts, may enter information describing one or more categories of physiological data that the experts consider to be significant or useful for detection of conditions; fields in graphical user interface 120 may provide options describing previously identified categories, which may include a comprehensive or near-comprehensive list of types of physiological data detectable using known or recorded testing methods, for instance in "drop-down" lists, where experts may be able to select one or more entries to indicate their usefulness and/or significance in the opinion of the experts. Fields may include free-form entry fields such as text-entry fields where an expert may be able to type or otherwise enter text, enabling expert to propose or suggest categories not currently recorded. Graphical user interface 120 or the like may include fields corresponding to prognostic labels, where experts may enter data describing prognostic labels and/or categories of prognostic labels the experts consider related to entered categories of physiological data; for instance, such fields may include drop-down lists or other pre-populated data entry fields listing currently recorded prognostic labels, and which may be comprehensive, permitting each expert to select a prognostic label and/or a plurality of prognostic labels the expert believes to be predicted and/or associated with each category of physiological data selected by the expert. Fields for entry of prognostic labels and/or categories of prognostic labels may include free-form data entry fields such as text entry fields; as described above, examiners may enter data not presented in pre-populated data fields in the free-form data entry fields. Alternatively or additionally, fields for entry of prognostic labels may enable an expert to select and/or enter information describing or linked to a category of prognostic label that the expert considers significant, where significance may indicate likely impact on longevity, mortality, quality of life, or the like as described in further detail below. Graphical user interface 120 may provide an expert with a field in which to indicate a reference to a document describing significant categories of physiological data, relationships of such categories to prognostic labels, and/or significant categories of prognostic labels. Any data described above may alternatively or additionally be received from experts similarly organized in paper form, which may be captured and entered into data in a similar way, or in a textual form such as a portable document file (PDF) with examiner entries, or the like Referring again to FIG. 1, data information describing significant categories of physiological data, relationships of such categories to prognostic labels, and/or significant categories of prognostic labels may alternatively or additionally be extracted from one or more documents using a language processing module 124. Language processing module 124 may include any hardware and/or software module. Language processing module 124 may be configured to extract, from the one or more documents, one or more words. One or more words may include, without limitation, strings of one or characters, including without limitation any sequence or sequences of letters, numbers, punctuation, diacritic marks, engineering symbols, geometric dimensioning and tolerancing (GD&T) symbols, chemical symbols and formulas, spaces, whitespace, and other symbols, including any symbols usable as textual data as described above. Textual data may be parsed into tokens, which may include a simple word (sequence of letters separated by whitespace) or more generally a sequence of characters as described previously. The term "token," as used herein, refers to any smaller, individual groupings of text from a larger source of text; tokens may be broken up by word, pair of words, sentence, or other delimitation. These tokens may in turn be parsed in various ways. Textual data may be parsed into words or sequences of words, which may be considered words as well. Textual data may be parsed into "n-grams", where all sequences of n consecutive characters are considered. Any or all possible sequences of tokens or words may be stored as "chains", for example for use as a Markov chain or Hidden Markov Model.

Still referring to FIG. 1, language processing module 124 may compare extracted words to categories of physiological data recorded at classification device 104, one or more prognostic labels recorded at classification device 104, and/or one or more categories of prognostic labels recorded at classification device 104; such data for comparison may be entered on classification device 104 as described above using expert data inputs or the like. In an embodiment, one or more categories may be enumerated, to find total count of mentions in such documents. Alternatively or additionally, language processing module 124 may operate to produce a language processing model. Language processing model may include a program automatically generated by classification device 104 and/or language processing module 124 to produce associations between one or more words extracted from at least a document and detect associations, including without limitation mathematical associations, between such words, and/or associations of extracted words with categories of physiological data, relationships of such categories to prognostic labels, and/or categories of prognostic labels. Associations between language elements, where language elements include for purposes herein extracted words, categories of physiological data, relationships of such categories to prognostic labels, and/or categories of prognostic labels may include, without limitation, mathematical associations, including without limitation statistical correlations between any language element and any other language element and/or language elements. Statistical correlations and/or mathematical associations may include probabilistic formulas or relationships indicating, for instance, a likelihood that a given extracted word indicates a given category of physiological data, a given relationship of such categories to prognostic labels, and/or a given category of prognostic labels. As a further example, statistical correlations and/or mathematical associations may include probabilistic formulas or relationships indicating a positive and/or negative association between at least an extracted word and/or a given category of physiological data, a given relationship of such categories to prognostic labels, and/or a given category of prognostic labels; positive or negative indication may include an indication that a given document is or is not indicating a category of physiological data, relationship of such category to prognostic labels, and/or category of prognostic labels is or is not significant. For instance, and without limitation, a negative indication may be determined from a phrase such as "telomere length was not found to be an accurate predictor of overall longevity," whereas a positive indication may be determined from a phrase such as "telomere length was found to be an accurate predictor of dementia," as an illustrative example; whether a phrase, sentence, word, or other textual element in a document or corpus of documents constitutes a positive or negative indicator may be determined, in an embodiment, by mathematical associations between detected words, comparisons to phrases and/or words indicating positive and/or negative indicators that are stored in memory at classification device 104, or the like.

Still referring to FIG. 1, language processing module 124 and/or classification device 104 may generate the language processing model by any suitable method, including without limitation a natural language processing classification algorithm; language processing model may include a natural language process classification model that enumerates and/or derives statistical relationships between input term and output terms. Algorithm to generate language processing model may include a stochastic gradient descent algorithm, which may include a method that iteratively optimizes an objective function, such as an objective function representing a statistical estimation of relationships between terms, including relationships between input terms and output terms, in the form of a sum of relationships to be estimated. In an alternative or additional approach, sequential tokens may be modeled as chains, serving as the observations in a Hidden Markov Model (HMM). HMMs as used herein are statistical models with inference algorithms that that may be applied to the models. In such models, a hidden state to be estimated may include an association between an extracted word category of physiological data, a given relationship of such categories to prognostic labels, and/or a given category of prognostic labels. There may be a finite number of category of physiological data, a given relationship of such categories to prognostic labels, and/or a given category of prognostic labels to which an extracted word may pertain, an HMM inference algorithm, such as the forward-backward algorithm or the Viterbi algorithm, may be used to estimate the most likely discrete state given a word or sequence of words. Language processing module 124 may combine two or more approaches. For instance, and without limitation, machine-learning program may use a combination of Naive-Bayes (NB), Stochastic Gradient Descent (SGD), and parameter grid-searching classification techniques; the result may include a classification algorithm that returns ranked associations.

Continuing to refer to FIG. 1, generating language processing model may include generating a vector space, which may be a collection of vectors, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each vector in an n-dimensional vector space may be represented by an n-tuple of numerical values. Each unique extracted word and/or language element as described above may be represented by a vector of the vector space. In an embodiment, each unique extracted and/or other language element may be represented by a dimension of vector space; as a non-limiting example, each element of a vector may include a number representing an enumeration of co-occurrences of the word and/or language element represented by the vector with another word and/or language element. Vectors may be normalized, scaled according to relative frequencies of appearance and/or file sizes. In an embodiment associating language elements to one another as described above may include computing a degree of vector similarity between a vector representing each language element and a vector representing another language element; vector similarity may be measured according to any norm for proximity and/or similarity of two vectors, including without limitation cosine similarity, which measures the similarity of two vectors by evaluating the cosine of the angle between the vectors, which can be computed using a dot product of the two vectors divided by the lengths of the two vectors. Degree of similarity may include any other geometric measure of distance between vectors.

Still referring to FIG. 1, language processing module 124 may use a corpus of documents to generate associations between language elements in a language processing module 124, and classification device 104 may then use such associations to analyze words extracted from one or more documents and determine that the one or more documents indicate significance of a category of physiological data, a given relationship of such categories to prognostic labels, and/or a given category of prognostic labels. In an embodiment, classification device 104 may perform this analysis using a selected set of significant documents, such as documents identified by one or more experts as representing good science, good clinical analysis, or the like; experts may identify or enter such documents via graphical user interface 120 as described above in reference to FIG. 9, or may communicate identities of significant documents according to any other suitable method of electronic communication, or by providing such identity to other persons who may enter such identifications into classification device 104. Documents may be entered into classification device 104 by being uploaded by an expert or other persons using, without limitation, file transfer protocol (FTP) or other suitable methods for transmission and/or upload of documents; alternatively or additionally, where a document is identified by a citation, a uniform resource identifier (URI), uniform resource locator (URL) or other datum permitting unambiguous identification of the document, classification device 104 may automatically obtain the document using such an identifier, for instance by submitting a request to a database or compendium of documents such as JSTOR as provided by Ithaka Harbors, Inc. of New York.

Continuing to refer to FIG. 1, whether an entry indicating significance of a category of physiological data, a given relationship of such categories to prognostic labels, and/or a given category of prognostic labels is entered via graphical user interface 120, alternative submission means, and/or extracted from a document or body of documents as described above, an entry or entries may be aggregated to indicate an overall degree of significance. For instance, each category of physiological data, relationship of such categories to prognostic labels, and/or category of prognostic labels may be given an overall significance score; overall significance score may, for instance, be incremented each time an expert submission and/or paper indicates significance as described above. Persons skilled in the art, upon reviewing the entirety of this disclosure will be aware of other ways in which scores may be generated using a plurality of entries, including averaging, weighted averaging, normalization, and the like. Significance scores may be ranked; that is, all categories of physiological data, relationships of such categories to prognostic labels, and/or categories of prognostic labels may be ranked according significance scores, for instance by ranking categories of physiological data, relationships of such categories to prognostic labels, and/or categories of prognostic labels higher according to higher significance scores and lower according to lower significance scores. Categories of physiological data, relationships of such categories to prognostic labels, and/or categories of prognostic labels may be eliminated from current use if they fail a threshold comparison, which may include a comparison of significance score to a threshold number, a requirement that significance score belong to a given portion of ranking such as a threshold percentile, quartile, or number of top-ranked scores. Significance scores may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated. Alternatively or additionally, significance scores may be calculated per sample type; for instance, entries by experts, documents, and/or descriptions of purposes of a given type of physiological test or sample collection as described above may indicate that for that type of physiological test or sample collection a first category of physiological data, relationship of such category to prognostic labels, and/or category of prognostic labels is significant with regard to that test, while a second category of physiological data, relationship of such category to prognostic labels, and/or category of prognostic labels is not significant; such indications may be used to perform a significance score for each category of physiological data, relationship of such category to prognostic labels, and/or category of prognostic labels is or is not significant per type of physiological sample, which then may be subjected to ranking, comparison to thresholds and/or elimination as described above.

Still referring to FIG. 1, classification device 104 may detect further significant categories of physiological data, relationships of such categories to prognostic labels, and/or categories of prognostic labels using machine-learning processes, including without limitation unsupervised machine-learning processes as described in further detail below; such newly identified categories, as well as categories entered by experts in free-form fields as described above, may be added to pre-populated lists of categories, lists used to identify language elements for language learning module, and/or lists used to identify and/or score categories detected in documents, as described above.

Continuing to refer to FIG. 1, in an embodiment, classification device 104 may be configured, for instance as part of receiving the first training set 108, to associate at least correlated first prognostic label 116 with at least a category from a list of significant categories of prognostic labels. Significant categories of prognostic labels may be acquired, determined, and/or ranked as described above. As a non-limiting example, prognostic labels may be organized according to relevance to and/or association with a list of significant conditions. A list of significant conditions may include, without limitation, conditions having generally acknowledged impact on longevity and/or quality of life; this may be determined, as a non-limiting example, by a product of relative frequency of a condition within the population with years of life and/or years of able-bodied existence lost, on average, as a result of the condition. A list of conditions may be modified for a given person to reflect a family history of the person; for instance, a person with a significant family history of a particular condition or set of conditions, or a genetic profile having a similarly significant association therewith, may have a higher probability of developing such conditions than a typical person from the general population, and as a result classification device 104 may modify list of significant categories to reflect this difference.

Still referring to FIG. 1, classification device 104 is designed and configured to receive a second training set 128 including a plurality of second data entries. Each second data entry of the second training set 128 includes at least a second prognostic label 132; at least a second prognostic label 132 may include any label suitable for use as at least a first prognostic label 116 as described above. Each data entry of the second training set 128 includes at least a correlated third prognostic label, where at least a third prognostic label 136 may include any label suitable for use as at least a first prognostic label 116 as described above; at least a third prognostic label 136 may be correlated with at least a second prognostic label 132 in any way described above for correlation of at least an element of physiological state data to at least a first prognostic label 116 as described above.

Continuing to refer to FIG. 1, in an embodiment classification device 104 may be configured, for instance as part of receiving second training set 128, to associate the at least second prognostic label and/or at least a third prognostic label 136 with at least a category from a list of significant categories of prognostic labels. This may be performed as described above for use of lists of significant categories with regard to at least a first prognostic label 116. Significance may be determined, and/or association with at least a category, may be performed for prognostic labels in first training set 108 according to a first process as described above and for prognostic labels in second training set 128 according to a second process as described above.

In an embodiment, and still referring to FIG. 1, classification device 104 may extract at least a second data entry from one or more documents; extraction may be performed using any language processing method as described above. Classification device 104 may be configured, for instance as part of receiving second training set 128, to receive at least a document describing at least a medical history and extract at least a second data entry of plurality of second data entries from the at least a document. A medical history document may include, for instance, a document received from an expert and/or medical practitioner describing treatment of a patient; document may be anonymized by removal of one or more patient-identifying features from document. A medical history document may include a case study, such as a case study published in a medical journal or written up by an expert. A medical history document may contain data describing and/or described by a prognostic label; for instance, the medical history document may list a diagnosis that a medical practitioner made concerning the patient, a finding that the patient is at risk for a given condition and/or evinces some precursor state for the condition, or the like. A medical history document may contain data describing and/or described by an additional prognostic label; for instance, the medical history document may list an underlying cause of a condition described by another prognostic label, a prognostic label associated with a co-related or simultaneously discovered condition and/or symptom, or the like. For instance, and without limitation, a medical professional may report that a first condition, associated with a second prognostic label, is caused wholly or in part by a second condition, associated with a third prognostic label; as a non-limiting illustration, a patient presenting with type II diabetes may also present with obesity, and a medical professional may enter a report describing the obesity as a cause of the type II diabetes. A medical history document may describe an outcome; for instance, medical history document may describe an improvement in a condition describing or described by a prognostic label, and/or may describe that the condition did not improve. For instance, and for illustrative purposes only, a patient presenting with type II diabetes and obesity may be described as losing weight, and a subsequent alleviation and/or cessation in diabetic symptoms may be observed and described in a medical report; a medical professional may further enter a conclusion, based on such observation, that obesity was a likely underlying cause of type II diabetes. Prognostic labels, correlations between prognostic labels, and/or causative relationships between prognostic labels, may be extracted from and/or determined from one or more medical history documents using any processes for language processing as described above; for instance, language processing module 124 may perform such processes. As a non-limiting example, positive and/or negative indications regarding prognostic labels and/or relationships therebetween as identified in medical history documents may be determined in a manner described above for determination of positive and/or negative indications regarding categories of physiological data, relationships of such categories to prognostic labels, and/or categories of prognostic labels.

With continued reference to FIG. 1, second training set 128 may include at least a data entry including at least a second element of physiological state data 140 and at least a correlated fourth prognostic label; the at least a data entry including at least a second element of physiological state data 140 and at least a correlated fourth prognostic label may include any data entry suitable for use as first data entries in first training set 108 as described above, and may be generated and/or received by any process suitable for generation and/or reception of first data entries in first training set 108. In an embodiment, inclusion in second training set 128 of at least a data entry including at least a second element of physiological state data 140 and at least a correlated fourth prognostic label permits determination of causal relationships between a prognostic label in combination with one or more elements of physiological data with another prognostic label, as described in further detail below.

In an embodiment, and still referring to FIG. 1, data entries in second training set 128 may be labeled and/or selected to indicate causal relationships; for instance, language processing module 124 may determine that an expert textual submission, medical report, or the like describes a causal relationship between a first prognostic label 116 and a second prognostic label, and may flag or otherwise indicate such a relationship in an entry in second training set 128. As a further non-limiting example, an expert may enter, in a graphical user interface 120 as described above, information indicative of a causal relationship between a first prognostic label 116 and a second prognostic label. Such a causal relationship may be stored in a causal link table of a prognostic label database as described in further detail below.

With continued reference to FIG. 1, classification device 104 may be configured, for instance as part of receiving second training set 128, to receiving at least a second data entry of the plurality of second data entries from at least an expert. This may be performed, without limitation, using second graphical user interface 120 as described above.

Figure 2:
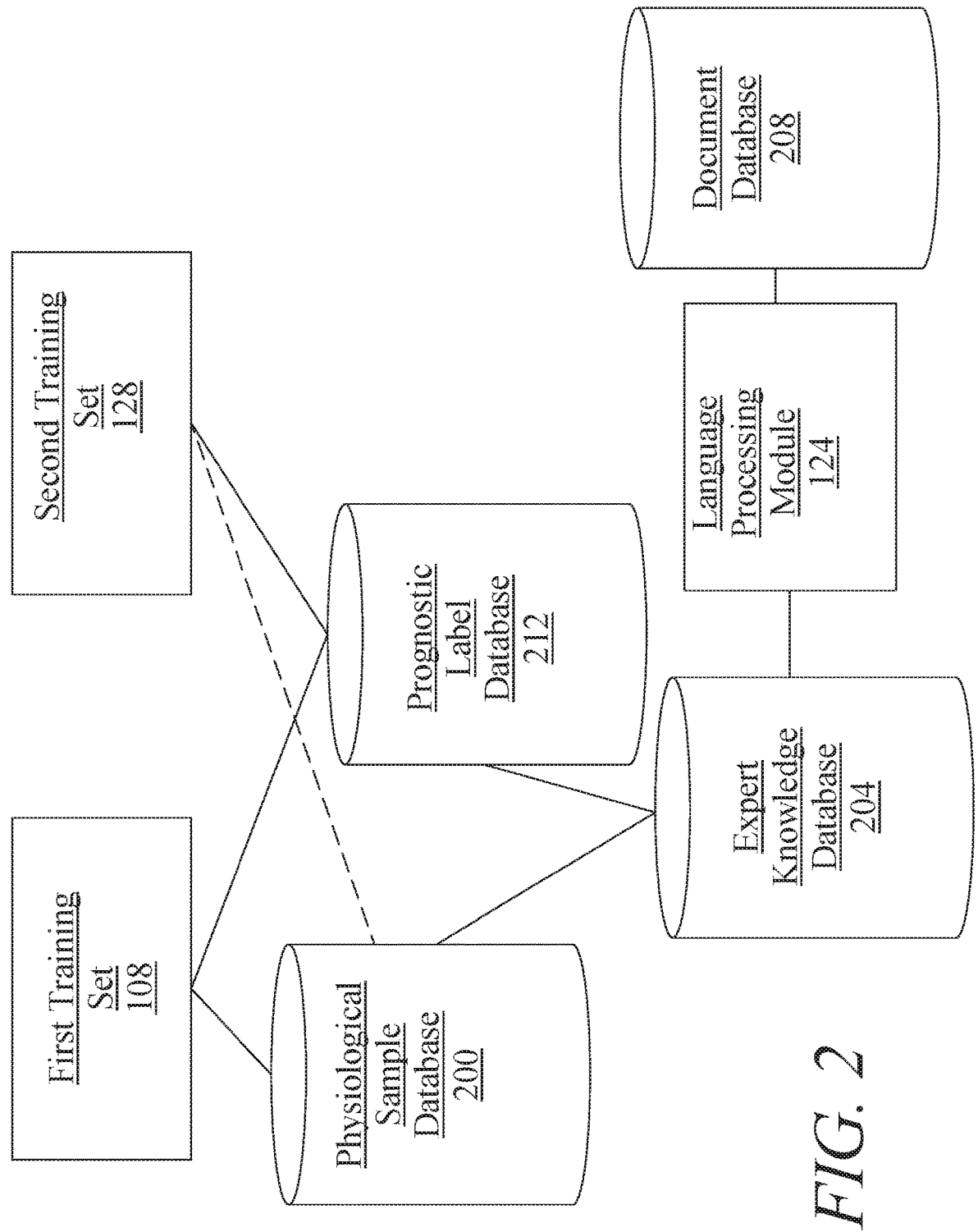
FIG. 2 is a block diagram illustrating embodiments of data storage facilities for use in disclosed systems and methods.

Referring now to FIG. 2, data incorporated in first training set 108 and/or second training set 128 may be incorporated in one or more databases. As a non-limiting example, one or elements of physiological state data may be stored in and/or retrieved from a physiological sample database 200. A physiological sample database 200 may include any data structure for ordered storage and retrieval of data, which may be implemented as a hardware or software module. A physiological sample database 200 may be implemented, without limitation, as a relational database, a key-value retrieval datastore such as a NOSQL database, or any other format or structure for use as a datastore that a person skilled in the art would recognize as suitable upon review of the entirety of this disclosure. A physiological sample database 200 may include a plurality of data entries and/or records corresponding to elements of physiological data as described above. Data entries and/or records may describe, without limitation, data concerning particular physiological samples that have been collected; entries may describe reasons for collection of samples, such as without limitation one or more conditions being tested for, which may be listed with related prognostic labels. Data entries may include prognostic labels and/or other descriptive entries describing results of evaluation of past physiological samples, including diagnoses that were associated with such samples, prognoses and/or conclusions regarding likelihood of future diagnoses that were associated with such samples, and/or other medical or diagnostic conclusions that were derived. Such conclusions may have been generated by system 100 in previous iterations of methods, with or without validation of correctness by medical professionals. Data entries in a physiological sample database 200 may be flagged with or linked to one or more additional elements of information, which may be reflected in data entry cells and/or in linked tables such as tables related by one or more indices in a relational database; one or more additional elements of information may include data associating a physiological sample and/or a person from whom a physiological sample was extracted or received with one or more cohorts, including demographic groupings such as ethnicity, sex, age, income, geographical region, or the like, one or more common diagnoses or physiological attributes shared with other persons having physiological samples reflected in other data entries, or the like. Additional elements of information may include one or more categories of physiological data as described above. Additional elements of information may include descriptions of particular methods used to obtain physiological samples, such as without limitation physical extraction of blood samples or the like, capture of data with one or more sensors, and/or any other information concerning provenance and/or history of data acquisition. Persons skilled in the art, upon reviewing the entirety of this disclosure, will be aware of various ways in which data entries in a physiological sample database 200 may reflect categories, cohorts, and/or populations of data consistently with this disclosure.

Figure 3:
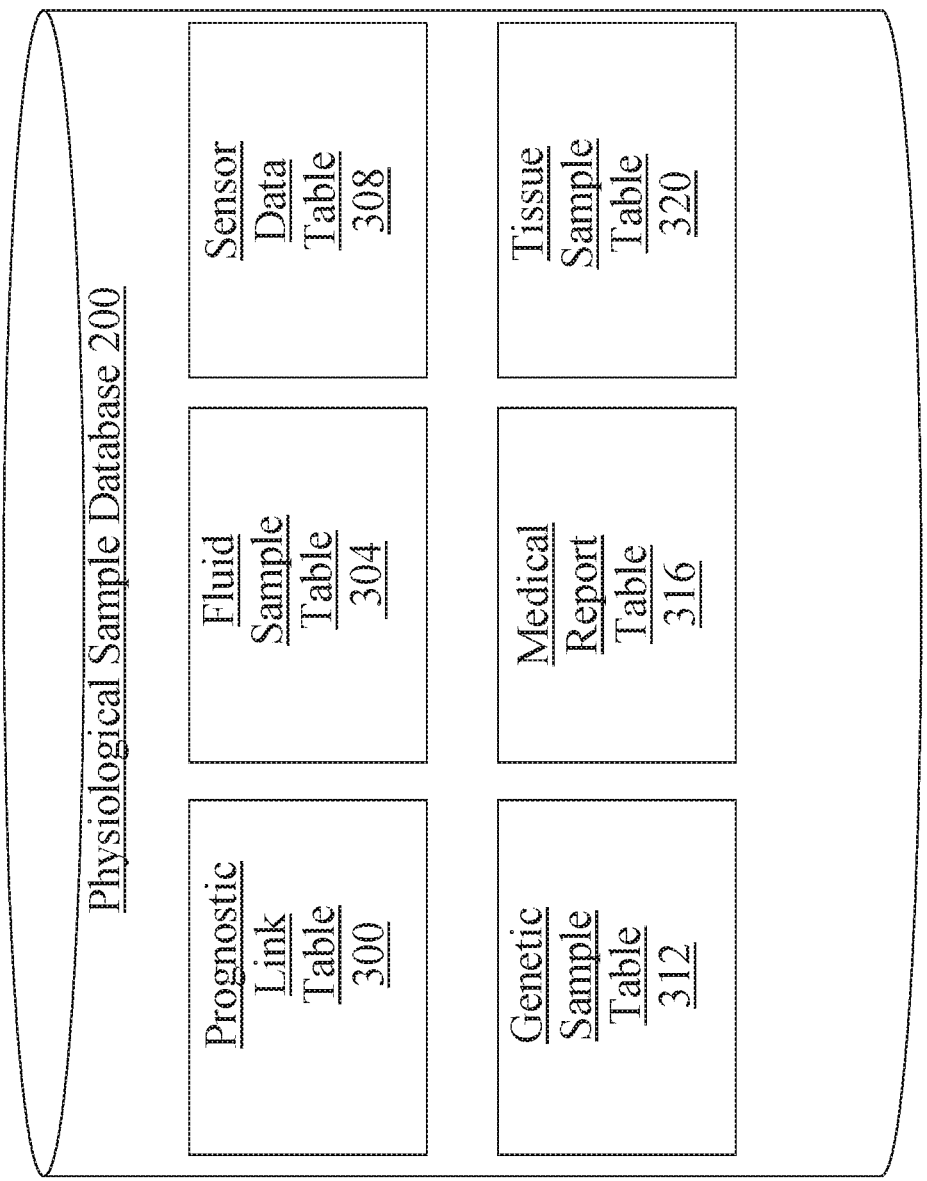
FIG. 3 is a block diagram illustrating an exemplary embodiment of a physiological sample database.

Referring now to FIG. 3, one or more database tables in physiological sample database 200 may include, as a non-limiting example, a prognostic link table 300. Prognostic link table 300 may be a table relating physiological sample data as described above to prognostic labels; for instance, where an expert has entered data relating a prognostic label to a category of physiological sample data and/or to an element of physiological sample data via first graphical user interface 120 as described above, one or more rows recording such an entry may be inserted in prognostic link table 300. Alternatively or additionally, linking of prognostic labels to physiological sample data may be performed entirely in a prognostic label database as described below.

With continued reference to FIG. 3, physiological sample database 200 may include tables listing one or more samples according to sample source. For instance, and without limitation, physiological sample database 200 may include a fluid sample table 304 listing samples acquired from a person by extraction of fluids, such as without limitation blood, lymph cerebrospinal fluid, or the like. As another non-limiting example, physiological sample database 200 may include a sensor data table 308, which may list samples acquired using one or more sensors, for instance as described in further detail below. As a further non-limiting example, physiological sample database 200 may include a genetic sample table 312, which may list partial or entire sequences of genetic material. Genetic material may be extracted and amplified, as a non-limiting example, using polymerase chain reactions (PCR) or the like. As a further example, also non-limiting, physiological sample database 200 may include a medical report table 316, which may list textual descriptions of medical tests, including without limitation radiological tests or tests of strength and/or dexterity or the like. Data in medical report table may be sorted and/or categorized using a language processing module 124 312, for instance, translating a textual description into a numerical value and a label corresponding to a category of physiological data; this may be performed using any language processing algorithm or algorithms as referred to in this disclosure. As another non-limiting example, physiological sample database 200 may include a tissue sample table 320, which may record physiological samples obtained using tissue samples. Tables presented above are presented for exemplary purposes only; persons skilled in the art will be aware of various ways in which data may be organized in physiological sample database 200 consistently with this disclosure.

Referring again to FIG. 2, classification device 104 and/or another device in system 100 may populate one or more fields in physiological sample database 200 using expert information, which may be extracted or retrieved from an expert knowledge database 204. An expert knowledge database 204 may include any data structure and/or data store suitable for use as a physiological sample database 200 as described above. Expert knowledge database 204 may include data entries reflecting one or more expert submissions of data such as may have been submitted according to any process described above in reference to FIG. 1, including without limitation by using first graphical user interface 120 and/or second graphical user interface 120. Expert knowledge database may include one or more fields generated by language processing module 124, such as without limitation fields extracted from one or more documents as described above. For instance, and without limitation, one or more categories of physiological data and/or related prognostic labels and/or categories of prognostic labels associated with an element of physiological state data as described above may be stored in generalized from in an expert knowledge database 204 and linked to, entered in, or associated with entries in a physiological sample database 200.

Documents may be stored and/or retrieved by classification device 104 and/or language processing module 124 in and/or from a document database 208; document database 208 may include any data structure and/or data store suitable for use as physiological sample database 200 as described above. Documents in document database 208 may be linked to and/or retrieved using document identifiers such as URI and/or URL data, citation data, or the like; persons skilled in the art, upon reviewing the entirety of this disclosure, will be aware of various ways in which documents may be indexed and retrieved according to citation, subject matter, author, date, or the like as consistent with this disclosure.

Figure 4:
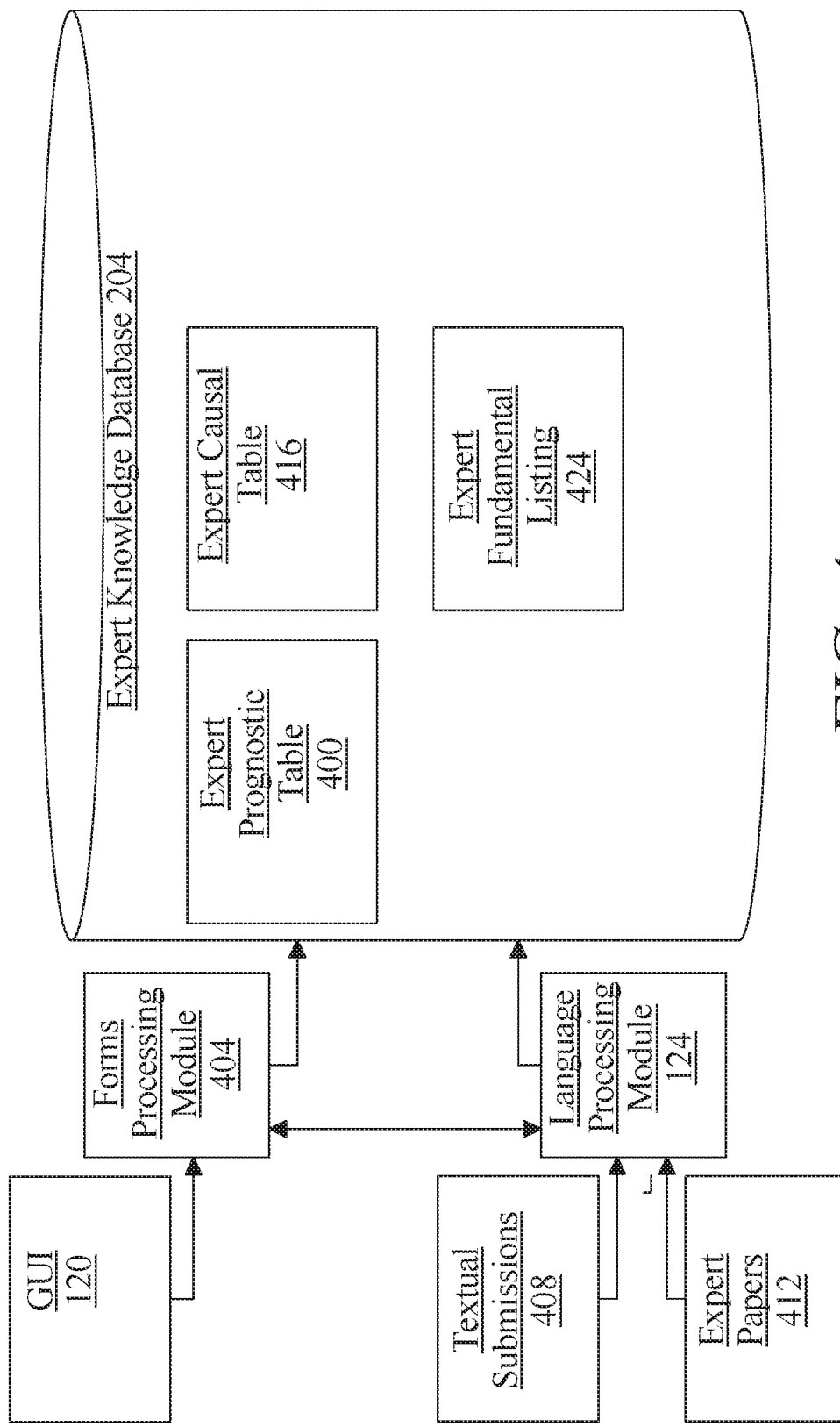
FIG. 4 is a block diagram illustrating an exemplary embodiment of an expert knowledge database.

Referring now to FIG. 4, an exemplary embodiment of an expert knowledge database 204 is illustrated. Expert knowledge database 204 may, as a non-limiting example, organize data stored in the expert knowledge database 204 according to one or more database tables. One or more database tables may be linked to one another by, for instance, common column values. For instance, a common column between two tables of expert knowledge database 200 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 4, one or more database tables in expert knowledge database 204 may include, as a non-limiting example, an expert prognostic table 400. Expert prognostic table 400 may be a table relating physiological sample data as described above to prognostic labels; for instance, where an expert has entered data relating a prognostic label to a category of physiological sample data and/or to an element of physiological sample data via first graphical user interface 120 as described above, one or more rows recording such an entry may be inserted in expert prognostic table 400. In an embodiment, a forms processing module 404 may sort data entered in a submission via first graphical user interface 120 by, for instance, sorting data from entries in the first graphical user interface 120 to related categories of data; for instance, data entered in an entry relating in the first graphical user interface 120 to a prognostic label may be sorted into variables and/or data structures for storage of prognostic labels, while data entered in an entry relating to a category of physiological data and/or an element thereof may be sorted into variables and/or data structures for the storage of, respectively, categories of physiological data or elements of physiological data. Where data is chosen by an expert from pre-selected entries such as drop-down lists, data may be stored directly; where data is entered in textual form, language processing module 124 may be used to map data to an appropriate existing label, for instance using a vector similarity test or other synonym-sensitive language processing test to map physiological data to an existing label. Alternatively or additionally, when a language processing algorithm, such as vector similarity comparison, indicates that an entry is not a synonym of an existing label, language processing module 124 may indicate that entry should be treated as relating to a new label; this may be determined by, e.g., comparison to a threshold number of cosine similarity and/or other geometric measures of vector similarity of the entered text to a nearest existent label, and determination that a degree of similarity falls below the threshold number and/or a degree of dissimilarity falls above the threshold number. Data from expert textual submissions 408, such as accomplished by filling out a paper or PDF form and/or submitting narrative information, may likewise be processed using language processing module 124. Data may be extracted from expert papers 412, which may include without limitation publications in medical and/or scientific journals, by language processing module 124 via any suitable process as described herein. Persons skilled in the art, upon reviewing the entirety of this disclosure, will be aware of various additional methods whereby novel terms may be separated from already-classified terms and/or synonyms therefore, as consistent with this disclosure. Expert prognostic table 400 may include a single table and/or a plurality of tables; plurality of tables may include tables for particular categories of prognostic labels such as a current diagnosis table, a future prognosis table, a genetic tendency table, a metabolic tendency table, and/or an endocrinal tendency table (not shown), to name a few non-limiting examples presented for illustrative purposes only.

With continued reference to FIG. 4, one or more database tables in expert knowledge database 204 may include, as a non-limiting example, an expert causal table 416. Expert causal table 416 may contain one or more records indicating causal relationships, as described above, between prognostic labels, as provided by expert input. For instance, where a textual submission, expert paper, and/or entry via graphical user interface 120 describes a condition associated with a first prognostic label as caused in part or fully by a second prognostic label, that information may be recorded in expert causal table 416. One or more database tables in expert knowledge database 204 may include, as a non-limiting example, an expert fundamental listing 424, which may contain entries that indicate one or more prognostic labels that at least an expert has identified as a root or fundamental cause of a condition associated with such labels and/or prognostic labels identified as caused by such labels.

Referring again to FIG. 2, a prognostic label database 212, which may be implemented in any manner suitable for implementation of physiological sample database 200, may be used to store prognostic labels used in system 100, including any prognostic labels correlated with elements of physiological data in first training set 108 as described above; prognostic labels may be linked to or refer to entries in physiological sample database 200 to which prognostic labels correspond. Linking may be performed by reference to historical data concerning physiological samples, such as diagnoses, prognoses, and/or other medical conclusions derived from physiological samples in the past; alternatively or additionally, a relationship between a prognostic label and a data entry in physiological sample database 200 may be determined by reference to a record in an expert knowledge database 204 linking a given prognostic label to a given category of physiological sample as described above. Entries in prognostic label database 212 may be associated with one or more categories of prognostic labels as described above, for instance using data stored in and/or extracted from an expert knowledge database 204.

Figure 5:
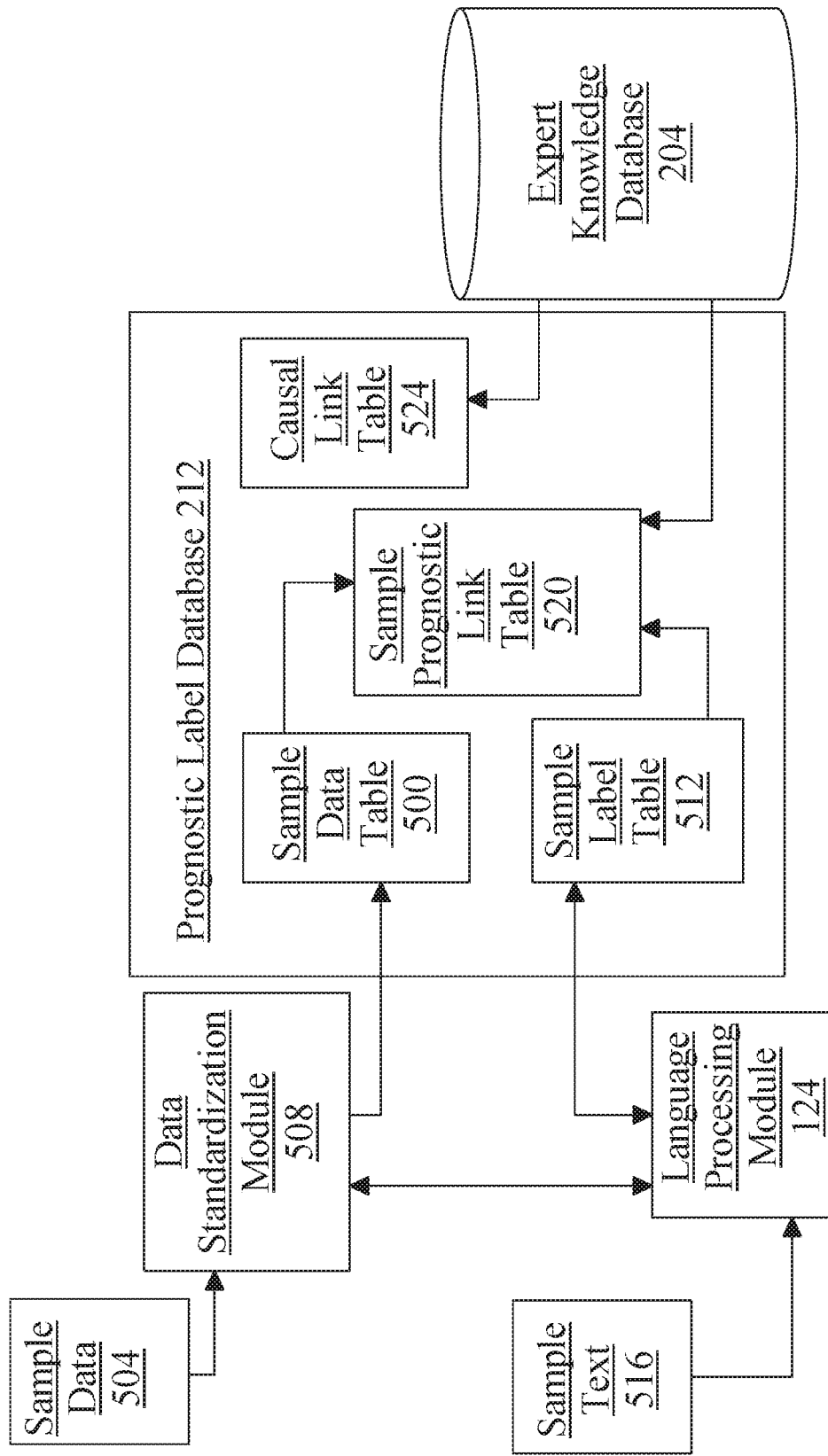
FIG. 5 is a block diagram illustrating an exemplary embodiment of a prognostic label database.

Referring now to FIG. 5, an exemplary embodiment of a prognostic label database 212 is illustrated. Prognostic label database 212 may, as a non-limiting example, organize data stored in the prognostic label database 212 according to one or more database tables. One or more database tables may be linked to one another by, for instance, common column values. For instance, a common column between two tables of prognostic label database 212 may include an identifier of an expert submission, such as a form entry, textual submission, expert paper, or the like, for instance as defined below; as a result, a query may be able to retrieve all rows from any table pertaining to a given submission or set thereof. Other columns may include any other category usable for organization or subdivision of expert data, including types of expert data, names and/or identifiers of experts submitting the data, times of submission, or the like; persons skilled in the art, upon reviewing the entirety of this disclosure, will be aware of various ways in which expert data from one or more tables may be linked and/or related to expert data in one or more other tables.

Still referring to FIG. 5, one or more database tables in prognostic label database 212 may include, as a non-limiting example, a sample data table 500. Sample data table 500 may be a table listing sample data, along with, for instance, one or more linking columns to link such data to other information stored in prognostic label database 212. In an embodiment, sample data 504 may be acquired, for instance from physiological sample database 200, in a raw or unsorted form, and may be translated into standard forms, such as standard units of measurement, labels associated with particular physiological data values, or the like; this may be accomplished using a data standardization module 508, which may perform unit conversions or the like. Data standardization module 508 may alternatively or additionally map textual information, such as labels describing values tested for or the like, using language processing module 124 or equivalent components and/or algorithms thereto.

Continuing to refer to FIG. 5, prognostic label database 212 may include a sample label table 512; sample label table 512 may list prognostic labels received with and/or extracted from physiological samples, for instance as received in the form of sample text 516. A language processing module 124 may compare textual information so received to prognostic labels and/or form new prognostic labels according to any suitable process as described above. A sample prognostic link table 520 may combine samples with prognostic labels, as acquired from sample label table 512 and/or expert knowledge database 204; combination may be performed by listing together in rows or by relating indices or common columns of two or more tables to each other. Tables presented above are presented for exemplary purposes only; persons skilled in the art will be aware of various ways in which data may be organized in expert knowledge database 204 consistently with this disclosure.

Still referring to FIG. 5, prognostic label database 212 may include a causal link table 524; causal link table 524 may identify, for a given prognostic label, one or more prognostic labels identifying potential causes of the given prognostic label. Causal link table 524 may be populated, as a non-limiting example, from expert knowledge database 424; for instance, and without limitation, classification device 104 may populate causal link table 524 using records from expert causal table 416.

Referring again to FIG. 2, first training set 108 may be populated by retrieval of one or more records from physiological sample database 200 and/or prognostic label database 212; in an embodiment, entries retrieved from physiological sample database 200 and/or prognostic label database 212 may be filtered and or select via query to match one or more additional elements of information as described above, so as to retrieve a first training set 108 including data belonging to a given cohort, demographic population, or other set, so as to generate outputs as described below that are tailored to a person or persons with regard to whom system 100 classifies physiological samples to prognostic labels as set forth in further detail below. Persons skilled in the art, upon reviewing the entirety of this disclosure, will be aware of various ways in which records may be retrieved from physiological sample database 200 and/or prognostic label database to generate a first training set 108 to reflect individualized group data pertaining to a person of interest in operation of system and/or method, including without limitation a person with regard to whom at least a physiological sample is being evaluated as described in further detail below. Classification device 104 may alternatively or additionally receive a first training set 108 and store one or more entries in physiological sample database 200 and/or prognostic label database 212 as extracted from elements of first training set 108.

Still referring to FIG. 2, second training set 128 may be populated by retrieval of one or more records from physiological sample database 200 and/or prognostic label database 212; in an embodiment, entries retrieved from physiological sample database 200 and/or prognostic label database 212 may be filtered and or select via query to match one or more additional elements of information as described above, so as to retrieve a second training set 128 including data belonging to a given cohort, demographic population, or other set, so as to generate outputs as described below that are tailored to a person or persons with regard to whom system 100 classifies physiological samples to prognostic labels as set forth in further detail below. Persons skilled in the art, upon reviewing the entirety of this disclosure, will be aware of various ways in which records may be retrieved from physiological sample database 200 and/or prognostic label database to generate a second training set 128 to reflect individualized group data pertaining to a person of interest in operation of system and/or method, including without limitation a person with regard to whom at least a physiological sample is being evaluated as described in further detail below. Classification device 104 may alternatively or additionally receive a second training set 128 and store one or more entries in physiological sample database 200 and/or prognostic label database 212 as extracted from elements of second training set 128.

In an embodiment, and still referring to FIG. 2, classification device 104 may receive an update to one or more elements of data represented in first training set 108 and/or second training set 128, and may perform one or more modifications to first training set 108 and/or second training set 128, or to physiological sample database 200, expert knowledge database 204, and/or prognostic label database 212 as a result. For instance a physiological sample may turn out to have been erroneously recorded; classification device 104 may remove it from first training set 108, second training set 128, physiological sample database 200, expert knowledge database 204, and/or prognostic label database 212 as a result. As a further example, a medical and/or academic paper, or a study on which it was based, may be revoked; classification device 104 may remove it from first training set 108, second training set 128, physiological sample database 200, expert knowledge database 204, and/or prognostic label database 212 as a result. Information provided by an expert may likewise be removed if the expert loses credentials or is revealed to have acted fraudulently.

Continuing to refer to FIG. 2, elements of data of first training set 108, second training set 128, physiological sample database 200, expert knowledge database 204, and/or prognostic label database 212 may have temporal attributes, such as timestamps; classification device 104 may order such elements according to recency, select only elements more recently entered for first training set 108 and/or second training set 128, or otherwise bias training sets, database entries, and/or machine-learning models as described in further detail below toward more recent or less recent entries. Persons skilled in the art, upon reviewing the entirety of this disclosure, will be aware of various ways in which temporal attributes of data entries may be used to affect results of methods and/or systems as described herein.

Referring again to FIG. 1, classification device 104 may be configured to record at least a first biological extraction. At least a first biological extraction may include any element and/or elements of data suitable for use as at least an element of physiological state data as described above. At least a biological extraction may include a physically extracted sample, where a "physically extracted sample" as used in this disclosure is a sample obtained by removing and analyzing tissue and/or fluid. Physically extracted sample may include without limitation a blood sample, a tissue sample, a buccal swab, a mucous sample, a stool sample, a hair sample, a fingernail sample, or the like. Physically extracted sample may include, as a non-limiting example, at least a blood sample. As a further non-limiting example, at least a biological extraction may include at least a genetic sample. At least a genetic sample may include a complete genome of a person or any portion thereof. At least a genetic sample may include a DNA sample and/or an RNA sample. At least a biological extraction may include an epigenetic sample, a proteomic sample, a tissue sample, a biopsy, and/or any other physically extracted sample. At least a biological extraction may include an endocrinal sample. As a further non-limiting example, the at least a biological extraction may include a signal from at least a sensor configured to detect physiological data of a user and recording the at least a biological extraction as a function of the signal. At least a sensor may include any medical sensor and/or medical device configured to capture sensor data concerning a patient, including any scanning, radiological and/or imaging device such as without limitation x-ray equipment, computer assisted tomography (CAT) scan equipment, positron emission tomography (PET) scan equipment, any form of magnetic resonance imagery (MRI) equipment, ultrasound equipment, optical scanning equipment such as photo-plethysmographic equipment, or the like. At least a sensor may include any electromagnetic sensor, including without limitation electroencephalographic sensors, magnetoencephalographic sensors, electrocardiographic sensors, electromyographic sensors, or the like. At least a sensor may include a temperature sensor. At least a sensor may include any sensor that may be included in a mobile device and/or wearable device, including without limitation a motion sensor such as an inertial measurement unit (IMU), one or more accelerometers, one or more gyroscopes, one or more magnetometers, or the like. At least a wearable and/or mobile device sensor may capture step, gait, and/or other mobility data, as well as data describing activity levels and/or physical fitness. At least a wearable and/or mobile device sensor may detect heart rate or the like. At least a sensor may detect any hematological parameter including blood oxygen level, pulse rate, heart rate, pulse rhythm, and/or blood pressure. At least a sensor may be a part of system 100 or may be a separate device in communication with system 100.

Still referring to FIG. 1, at least a first biological extraction may include data describing one or more test results, including results of mobility tests, stress tests, dexterity tests, endocrinal tests, genetic tests, and/or electromyographic tests, biopsies, radiological tests, genetic tests, and/or sensory tests. Persons skilled in the art, upon reviewing the entirety of this disclosure, will be aware of various additional examples of at least a physiological sample consistent with this disclosure. At least a physiological sample may be added to physiological sample database 200.

Continuing to refer to FIG. 1, system 100 includes a prognostic label learner 144 operating on classification device 104, the prognostic label learner 144 designed and configured to generate at least a first prognostic output as a function of the first training set 108 and the at least a biological extraction. Prognostic label learner 144 may include any hardware and/or software module. Prognostic label learner 144 is designed and configured to generate outputs using machine learning processes. A machine learning process is a process that automatedly uses a body of data known as "training data" and/or a "training set" to generate an algorithm that will be performed by a computing device/module to produce outputs given data provided as inputs; this is in contrast to a non-machine learning software program where the commands to be executed are determined in advance by a user and written in a programming language.

Still referring to FIG. 1, prognostic label learner 144 may be designed and configured to generate at least a prognostic output by creating at least a first machine-learning model 148 relating physiological state data to prognostic labels using the first training set 108 and generating the at least a prognostic output using the first machine-learning model 148; at least a first machine-learning model 148 may include one or more models that determine a mathematical relationship between physiological state data and prognostic labels. Such models may include without limitation model developed using linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure. Machine-learning may include other regression algorithms, including without limitation polynomial regression.

Continuing to refer to FIG. 1, machine-learning algorithm used to generate first machine-learning model 148 may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Still referring to FIG. 1, prognostic label learner 144 may generate prognostic output using alternatively or additional artificial intelligence methods, including without limitation by creating an artificial neural network, such as a convolutional neural network comprising an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. This network may be trained using first training set 108; the trained network may then be used to apply detected relationships between elements of physiological state data and prognostic labels.

Figure 6:
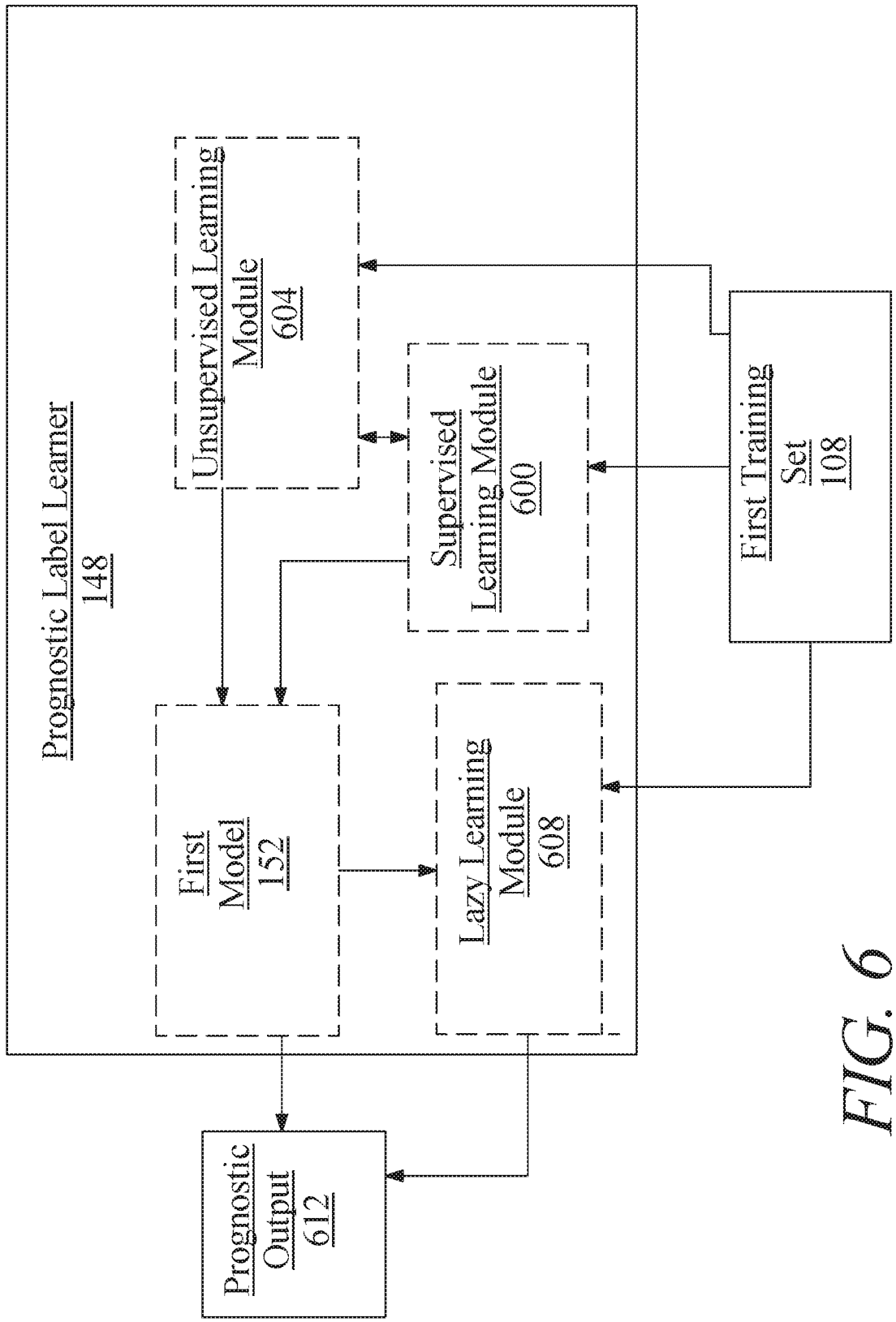
FIG. 6 is a block diagram illustrating an exemplary embodiment of a prognostic label learner and associated system elements.

Referring now to FIG. 6, machine-learning algorithms used by prognostic label learner 144 may include supervised machine-learning algorithms, which may, as a non-limiting example be executed using a supervised learning module 600 executing on classification device 104 and/or on another computing device in communication with classification device 104, which may include any hardware or software module. Supervised machine learning algorithms, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may use elements of physiological data as inputs, prognostic labels as outputs, and a scoring function representing a desired form of relationship to be detected between elements of physiological data and prognostic labels; scoring function may, for instance, seek to maximize the probability that a given element of physiological state data and/or combination of elements of physiological data is associated with a given prognostic label and/or combination of prognostic labels to minimize the probability that a given element of physiological state data and/or combination of elements of physiological state data is not associated with a given prognostic label and/or combination of prognostic labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set 108. Persons skilled in the art, upon reviewing the entirety of this disclosure, will be aware of various possible variations of supervised machine learning algorithms that may be used to determine relation between elements of physiological data and prognostic labels. In an embodiment, one or more supervised machine-learning algorithms may be restricted to a particular domain for instance, a supervised machine-learning process may be performed with respect to a given set of parameters and/or categories of parameters that have been suspected to be related to a given set of prognostic labels, and/or are specified as linked to a medical specialty and/or field of medicine covering a particular set of prognostic labels. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate prognostic labels. Additional supervised learning processes may be performed without domain restrictions to detect, for instance, previously unknown and/or unsuspected relationships between physiological data and prognostic labels.

Still referring to FIG. 6, machine-learning algorithms may include unsupervised processes; unsupervised processes may, as a non-limiting example, be executed by an unsupervised learning module 604 executing on classification device 104 and/or on another computing device in communication with classification device 104, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, prognostic label learner 144 and/or classification device 104 may perform an unsupervised machine learning process on first training set 108, which may cluster data of first training set 108 according to detected relationships between elements of the first training set 108, including without limitation correlations of elements of physiological state data to each other and correlations of prognostic labels to each other; such relations may then be combined with supervised machine learning results to add new criteria for prognostic label learner 144 to apply in relating physiological state data to prognostic labels. As a non-limiting, illustrative example, an unsupervised process may determine that a first element of physiological state data 112 acquired in a blood test correlates closely with a second element of physiological state data, where the first element has been linked via supervised learning processes to a given prognostic label, but the second has not; for instance, the second element may not have been defined as an input for the supervised learning process, or may pertain to a domain outside of a domain limitation for the supervised learning process. Continuing the example a close correlation between first element of physiological state data and second element of physiological state data may indicate that the second element is also a good predictor for the prognostic label; second element may be included in a new supervised process to derive a relationship or may be used as a synonym or proxy for the first physiological element by prognostic label learner 144.

Still referring to FIG. 6, classification device 104 and/or prognostic label learner 144 may detect further significant categories of physiological data, relationships of such categories to prognostic labels, and/or categories of prognostic labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, prognostic label learner 144 and/or classification device 104 may continuously or iteratively perform unsupervised machine-learning processes to detect relationships between different elements of the added and/or overall data; in an embodiment, this may enable system 100 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular prognostic labels and/or suitable ameliorative labels. Use of unsupervised learning may greatly enhance the accuracy and detail with which system may detect prognostic labels and/or ameliorative labels.

With continued reference to FIG. 6, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of prognostic label, and/or a group of people having a shared value and/or category of ameliorative label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 6, prognostic label learner 144 may alternatively or additionally be designed and configured to generate at least a prognostic output by executing a lazy learning process as a function of the first training set 108 and the at least a biological extraction; lazy learning processes may be performed by a lazy learning module 608 executing on classification device 104 and/or on another computing device in communication with classification device 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a prognostic label associated with biological extraction, using first training set 108. As a non-limiting example, an initial heuristic may include a ranking of prognostic labels according to relation to a test type of at least a biological extraction, one or more categories of physiological data identified in test type of at least a biological extraction, and/or one or more values detected in at least a biological extraction; ranking may include, without limitation, ranking according to significance scores of associations between elements of physiological data and prognostic labels, for instance as calculated as described above. Heuristic may include selecting some number of highest-ranking associations and/or prognostic labels. Prognostic label learner 144 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate prognostic outputs as described in this disclosure, including without limitation lazy learning applications of machine-learning algorithms as described in further detail below.

In an embodiment, and continuing to refer to FIG. 6, prognostic label learner 144 may generate a plurality of prognostic labels having different implications for a particular person. For instance, where the at least a physiological sample includes a result of a dexterity test, a low score may be consistent with amyotrophic lateral sclerosis, Parkinson's disease, multiple sclerosis, and/or any number of less sever disorders or tendencies associated with lower levels of dexterity. In such a situation, prognostic label learner 144 and/or classification device 104 may perform additional processes to resolve ambiguity. Processes may include presenting multiple possible results to a medical practitioner, informing the medical practitioner that one or more follow-up tests and/or physiological samples are needed to further determine a more definite prognostic label. Alternatively or additionally, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, prognostic label learner 144 and/or classification device 104 may operate a further algorithm to determine which of the multiple outputs is most likely to be correct; algorithm may include use of an additional supervised and/or unsupervised model. Alternatively or additionally, prognostic label learner 144 may perform one or more lazy learning processes using a more comprehensive set of user data to identify a more probably correct result of the multiple results. Results may be presented and/or retained with rankings, for instance to advise a medical professional of the relative probabilities of various prognostic labels being correct; alternatively or additionally, prognostic labels associated with a probability of correctness below a given threshold and/or prognostic labels contradicting results of the additional process, may be eliminated. As a non-limiting example, an endocrinal test may determine that a given person has high levels of dopamine, indicating that a poor pegboard performance is almost certainly not being caused by Parkinson's disease, which may lead to Parkinson's being eliminated from a list of prognostic labels associated with poor pegboard performance, for that person. Similarly, a genetic test may eliminate Huntington's disease, or another disease definitively linked to a given genetic profile, as a cause. Persons skilled in the art, upon reviewing the entirety of this disclosure, will be aware of various ways in which additional processing may be used to determine relative likelihoods of prognostic labels on a list of multiple prognostic labels, and/or to eliminate some labels from such a list. Prognostic output 612 may be provided to a user output device as described in further detail below.

Referring again to FIG. 1, classification device 104 includes a causal link learner 152 operating on the classification device 104, the causal link learner 152 designed and configured to generate the at least a second prognostic output 712 as a function of the second training set 128 and the at least a first prognostic output. Causal link learner 152 may generate a second machine-learning model 156 to generate the at least a second prognostic output 712, where second machine-learning model 156 may be generated using any process or combination of processes suitable for generation of first machine-learning model 148 as described above. At least a second prognostic output 712 may be causally linked to at least a first prognostic output. As used herein, at least a second prognostic output 712 is "causally linked" to at least a first prognostic output if a prognostic label in at least a second prognostic output 712 identifies a potential cause of a prognostic label in at least a first prognostic output, and/or a prognostic label in at least a first prognostic output identifies a potential cause of a prognostic label in at least a second prognostic output 712. A "potential cause," as used in the above definition of "causally linked" indicates a first phenomenon, such as physiological condition or other condition that may be labeled using a prognostic label, that has been identified as causing a second phenomenon, such as a physiological condition or other condition that may be labeled using a prognostic label, in at least one case; the first phenomenon, and/or the prognostic label associated therewith, is described for purposes herein as a "potential cause" for the second phenomenon. For instance, a genetic condition or mutation that causes elevated cholesterol in the blood of persons possessing that genetic condition or mutation is a "potential cause" of hypercholesterolemia, as it has been identified in some cases as causing the latter condition, while not necessarily being a cause in all cases. In an embodiment, at least a second prognostic output 712 may represent a cause of the at least a first prognostic output, which indicates, as used herein, that a prognostic label in at least a second prognostic output 712 identifies a potential cause of a prognostic label in at least a first prognostic output.

Figure 7:
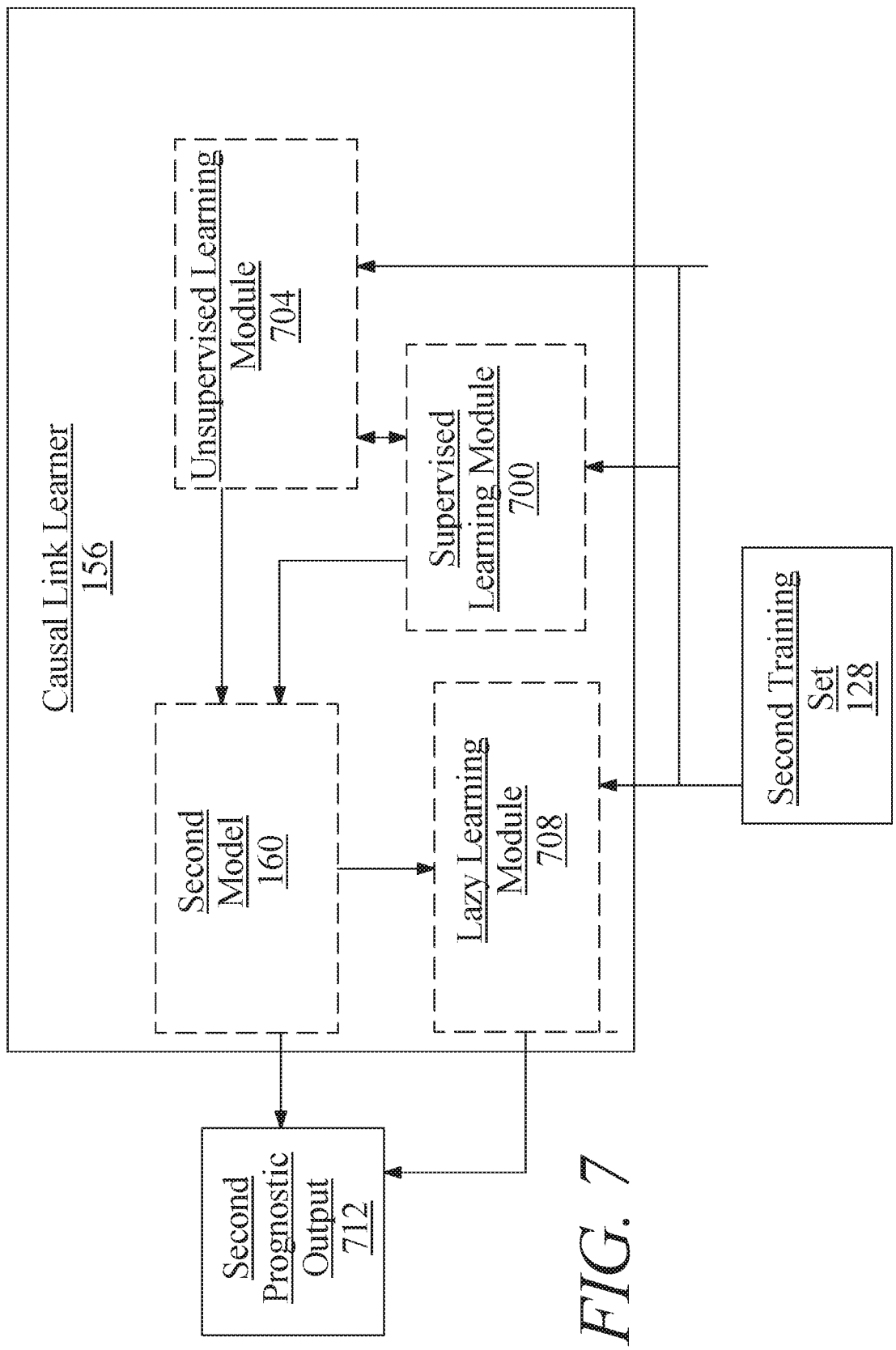
FIG. 7 is a block diagram illustrating an exemplary embodiment of an ameliorative process label learner and associated system elements.

Referring now to FIG. 7, machine-learning algorithms used by causal link learner 152 may include supervised machine-learning algorithms, which may, as a non-limiting example be executed using a supervised learning module 700 executing on classification device 104 and/or on another computing device in communication with classification device 104, which may include any hardware or software module; supervised learning may be performed as described above in reference to FIG. 6. For instance, a supervised learning algorithm may use at least a first prognostic output, prognostic labels from at least a first prognostic output, and/or elements of physiological data as inputs, prognostic labels as outputs, and a scoring function representing a desired form of relationship to be detected between at least a first prognostic output, one or more prognostic labels from at least a first prognostic output, and/or elements of physiological data and prognostic labels; scoring function may, for instance, seek to maximize the probability that a given first prognostic label 116 and/or element of physiological state data and/or combination of elements of physiological data is associated with a given second prognostic label and/or combination of prognostic labels to minimize the probability that a given first prognostic label 116 and/or element of physiological state data and/or combination of elements of physiological state data is not associated with a given prognostic label and/or combination of prognostic labels. Scoring function may be expressed as a risk function representing an "expected loss" of an algorithm relating inputs to outputs, where loss is computed as an error function representing a degree to which a prediction generated by the relation is incorrect when compared to a given input-output pair provided in first training set 108. Persons skilled in the art, upon reviewing the entirety of this disclosure, will be aware of various possible variations of supervised machine learning algorithms that may be used to determine relation between elements of physiological data and prognostic labels. In an embodiment, one or more supervised machine-learning algorithms may be restricted to a particular domain for instance, a supervised machine-learning process may be performed with respect to a given set of parameters and/or categories of parameters that have been suspected to be related to a given set of prognostic labels, and/or are specified as linked to a medical specialty and/or field of medicine covering a particular set of prognostic labels. As a non-limiting example, a particular set of blood test biomarkers and/or sensor data may be typically used by cardiologists to diagnose or predict various cardiovascular conditions, and a supervised machine-learning process may be performed to relate those blood test biomarkers and/or sensor data to the various cardiovascular conditions; in an embodiment, domain restrictions of supervised machine-learning procedures may improve accuracy of resulting models by ignoring artifacts in training data. Domain restrictions may be suggested by experts and/or deduced from known purposes for particular evaluations and/or known tests used to evaluate prognostic labels. Additional supervised learning processes may be performed without domain restrictions to detect, for instance, previously unknown and/or unsuspected relationships between physiological data and prognostic labels.

Still referring to FIG. 7, machine-learning algorithms may include unsupervised processes; unsupervised processes may, as a non-limiting example, be executed by an unsupervised learning module 704 executing on classification device 104 and/or on another computing device in communication with classification device 104, which may include any hardware or software module. An unsupervised machine-learning process, as used herein, is a process that derives inferences in datasets without regard to labels; as a result, an unsupervised machine-learning process may be free to discover any structure, relationship, and/or correlation provided in the data. For instance, and without limitation, causal link learner 152 and/or classification device 104 may perform an unsupervised machine learning process on first training set 108, which may cluster data of first training set 108 according to detected relationships between elements of the first training set 108, including without limitation correlations of elements of physiological state data to each other and/or correlations of prognostic labels to each other; such relations may then be combined with supervised machine learning results to add new criteria for causal link learner 152 to apply in relating physiological state data to prognostic labels.

Still referring to FIG. 7, classification device 104 and/or causal link learner 152 may detect further significant categories of physiological data, relationships of such categories to prognostic labels, and/or categories of prognostic labels using machine-learning processes, including without limitation unsupervised machine-learning processes as described above; such newly identified categories, as well as categories entered by experts in free-form fields as described above, may be added to pre-populated lists of categories, lists used to identify language elements for language learning module, and/or lists used to identify and/or score categories detected in documents, as described above. In an embodiment, as additional data is added to system 100, causal link learner 152 and/or classification device 104 may continuously or iteratively perform unsupervised machine-learning processes to detect relationships between different elements of the added and/or overall data; in an embodiment, this may enable system 100 to use detected relationships to discover new correlations between known biomarkers, prognostic labels, and/or ameliorative labels and one or more elements of data in large bodies of data, such as genomic, proteomic, and/or microbiome-related data, enabling future supervised learning and/or lazy learning processes as described in further detail below to identify relationships between, e.g., particular clusters of genetic alleles and particular prognostic labels. Use of unsupervised learning may greatly enhance the accuracy and detail with which system may detect prognostic labels and/or ameliorative labels.

With continued reference to FIG. 7, unsupervised processes may be subjected to domain limitations. For instance, and without limitation, an unsupervised process may be performed regarding a comprehensive set of data regarding one person, such as a comprehensive medical history, set of test results, and/or physiological data such as genomic, proteomic, and/or other data concerning that persons. As another non-limiting example, an unsupervised process may be performed on data concerning a particular cohort of persons; cohort may include, without limitation, a demographic group such as a group of people having a shared age range, ethnic background, nationality, sex, and/or gender. Cohort may include, without limitation, a group of people having a shared value for an element and/or category of physiological data, a group of people having a shared value for an element and/or category of prognostic label, and/or a group of people having a shared value and/or category of ameliorative label; as illustrative examples, cohort could include all people having a certain level or range of levels of blood triglycerides, all people diagnosed with type II diabetes, all people who regularly run between 10 and 15 miles per week, or the like. Persons skilled in the art, upon reviewing the entirety of this disclosure, will be aware of a multiplicity of ways in which cohorts and/or other sets of data may be defined and/or limited for a particular unsupervised learning process.

Still referring to FIG. 7, causal link learner 152 may alternatively or additionally be designed and configured to generate at least a second prognostic output 712 by executing a lazy learning process as a function of the first training set 108 and the at least a biological extraction; lazy learning processes may be performed by a lazy learning module 708 executing on classification device 104 and/or on another computing device in communication with classification device 104, which may include any hardware or software module. A lazy-learning process and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover a "first guess" at a second prognostic label associated with and or potentially causing a first prognostic label 116, using second training set 128. As a non-limiting example, an initial heuristic may include a ranking of prognostic labels according to a given prognostic label in first prognostic output, one or more categories associated with a given prognostic label in first prognostic output, or the like; ranking may include, without limitation, ranking according to significance scores of associations between prognostic labels, for instance as calculated as described above. Heuristic may include selecting some number of highest-ranking associations and/or prognostic labels. Causal link learner 152 may alternatively or additionally implement any suitable "lazy learning" algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate prognostic outputs as described in this disclosure, including without limitation lazy learning applications of machine-learning algorithms as described in further detail below. At least a second prognostic output 712 712 may be provided to a user output device as described in further detail below.

Referring again to FIG. 1, classification device 104 may be configured to transmit an output including at least a first prognostic output and at least a second prognostic output 712 712 to a user output device 160. A user output device 160 may include, without limitation, a display in communication with classification device 104; display may include any display as described in this disclosure. A user output device 160 may include an addition computing device, such as a mobile device, laptop, desktop computer, or the like; as a non-limiting example, the user output device 160 may be a computer and/or workstation operated by a medical professional. Output may be displayed on at least a user output device 160 using an output graphical user interface 120; output graphical user interface 120 may display one or more prognostic labels of at least a first prognostic output and/or at least a second prognostic output 712. Alternatively or additionally, prognostic labels may be translated into display data including without limitation textual descriptions corresponding to prognostic labels, one or more images associated with prognostic labels, and/or one or more video or audio files associated with prognostic labels; each of the above-described display data may be retrieved from a display data store, which may, for instance associate or link prognostic labels and/or elements of physiological data with one or more display data. Where output includes multiple prognostic labels, classification device 104 may cause to a user output device 160 to display the multiple labels and/or display data associated therewith; labels may be displayed according to rankings as described above, including without limitation rankings of prognostic labels according to probability of correctness or the like. Significance scores, as calculated above, may be used to filter outputs as described in further detail below; for instance, where a number of outputs are generated and automated selection of a smaller number of outputs is desired, outputs corresponding to higher significance scores may be identified as more probable and/or selected for presentation while other outputs corresponding to lower significance scores may be eliminated.

With continued reference to FIG. 1, classification device 104 may display one or more elements of contextual information, including without limitation any patient medical history such as current lab results, a current reason for visiting a medical professional, current status of one or more currently implemented treatment plans, biographical information concerning the patient, and the like. One or more elements of contextual information may include goals a patient wishes to achieve with a medical visit or session, and/or as result of interaction with system 100. Contextual information may include one or more questions a patient wishes to have answered in a medical visit and/or session, and/or as a result of interaction with system 100. Contextual information may include one or more questions to ask a patient. Persons skilled in the art, upon reviewing the entirety of this disclosure, will be aware of various forms of contextual information that may be included, consistently with this disclosure. System 100 may record a conversation between a patient and a medical professional for later entry into medical records.

With continued reference to FIG. 1, classification device 104 may be configured to display one or more follow-up suggestions at a user output device 160. One of more follow-up suggestions may include, without limitation, suggestions for acquisition of an additional biological extraction; in an embodiment, additional biological extraction may be provided to classification device 104, which may trigger repetition of one or more processes as described above, including without limitation generation of prognostic output, refinement or elimination of ambiguous prognostic labels of prognostic output, generation of ameliorative output, and/or refinement or elimination of ambiguous ameliorative labels of ameliorative output. For instance, where a pegboard test result suggests possible diagnoses of Parkinson's disease, Huntington's disease, ALS, and MS as described above, follow-up suggestions may include suggestions to perform endocrinal tests, genetic tests, and/or electromyographic tests; results of such tests may eliminate one or more of the possible diagnoses, such that a subsequently displayed output only lists conditions that have not been eliminated by the follow-up test. Follow-up tests may include any receipt of any physiological sample as described above.

In an embodiment, and still referring to FIG. 1, causal link learner 152 may output more than one second prognostic output 712; for instance, at least a first prognostic output may have more than one associated prognostic labels indicative of causes for conditions identified by at least a first prognostic label 116. In some cases such a multiplicity of potential causes may indicate that multiple factors are contributing to a cause of at least a first prognostic output; system 100 and/or classification device 104 may display multiple second prognostic outputs 712 to a user such as a medical professional, or may repeat one or more method steps as described in this disclosure to iterate from multiple second prognostic outputs 712 to third or additional prognostic outputs associated with fundamental or root causes, for instance by locating one or more causally linked fundamental prognostic labels. Alternatively or additionally, classification device 104 and/or system 100 may be configured to select a second prognostic output 712 from the plurality of second prognostic outputs 712; system 100 and/or classification device 104 may select one or more second prognostic outputs 712 from plurality of prognostic outputs, where selection may indicate a higher current degree of importance for ameliorative or alleviative purposes and/or elimination of one or more potential causes that are incorrect choices in this case. As a non-limiting example, a person complaining of joint pain may be linked to a first prognostic output associated with joint inflammation, which may in turn be linked, via causal link learner 152, to one second prognostic output 712 associated with gout and another second prognostic output 712 associated with rheumatoid arthritis; the person may be suffering from the latter and not the former, and system 100 may engage in one or more processes to select a correct second prognostic label.

With continued reference to FIG. 1, processes may include additional machine learning steps; for instance, where reference to a model generated using supervised learning on a limited domain has produced multiple mutually exclusive results and/or multiple results that are unlikely all to be correct, or multiple different supervised machine learning models in different domains may have identified mutually exclusive results and/or multiple results that are unlikely all to be correct. In such a situation, causal link learner 152 and/or classification device 104 may operate a further algorithm to determine which of the multiple outputs is most likely to be correct; algorithm may include use of an additional supervised and/or unsupervised model. Alternatively or additionally, causal link learner 152 may perform one or more lazy learning processes using a more comprehensive set of user data to identify a more probably correct result of the multiple results. Results may be presented and/or retained with rankings, for instance to advise a medical professional of the relative probabilities of various prognostic labels being correct; alternatively or additionally, prognostic labels associated with a probability of correctness below a given threshold and/or prognostic labels contradicting results of the additional process, may be eliminated. As a non-limiting example, an endocrinal test may determine that a given person has high levels of dopamine, indicating that a poor pegboard performance is almost certainly not being caused by Parkinson's disease, which may lead to Parkinson's being eliminated from a list of prognostic labels associated with poor pegboard performance, for that person. Similarly, a genetic test may eliminate Huntington's disease, or another disease definitively linked to a given genetic profile, as a cause. Persons skilled in the art, upon reviewing the entirety of this disclosure, will be aware of various ways in which additional processing may be used to determine relative likelihoods of prognostic labels on a list of multiple prognostic labels, and/or to eliminate some labels from such a list.

As a further non-limiting example, and still referring to FIG. 1, classification device 104 is further configured to receive at least a second biological extraction and select the second prognostic output 712 from the plurality of second prognostic outputs 712 as a function of the at least a second biological extraction; at least a second biological extraction may include any data suitable for use as at least a first biological extraction as described above. In an embodiment, at least a second biological extraction may be used directly to filter plurality of second prognostic outputs 712; for instance, a given prognostic label in second prognostic output 712 may be listed in prognostic link table of physiological sample database as associated with a particular result of a test or a particular value as determined by at least a second biological extraction, such that classification device 104 may select the prognostic label as matching, or reject the prognostic label as not matching, the at least a second biological extraction. As a non-limiting, illustrative example, where at least a second prognostic output 712 include one prognostic output associated with gout as a cause of joint inflammation as identified in at least a first prognostic output and another prognostic output associated with rheumatoid arthritis as a cause of the joint inflammation, prognostic link table may indicate that the former is associated with elevated urea levels; classification device 104 may therefore eliminate gout from at least a second prognostic output 712 where at least a second biological extraction indicates a low level of urea.

Alternatively or additionally, and still referring to FIG. 1, prognostic label learner 144 may be further configured to generate a third prognostic output as a function of the first training set 108 and the at least a second biological extraction; this may be performed, without limitation, as described above. Classification device 104 may be further configured to select a second prognostic output 712 from a plurality of second prognostic outputs 712 as a function of the third prognostic output. Selection may include selecting a second prognostic output 712 by determining that the second prognostic output 712 matches third prognostic output; for instance, and without limitation, causal link learner 152 may generate an additional output matching a second prognostic output 712, indicating that the second prognostic output 712 is a likely correct answer, and/or third prognostic output may itself match an output of second prognostic output 712. Selecting may include selecting a second prognostic output 712 by determining that a prognostic output of a plurality of second prognostic outputs 712 contradicts a third prognostic output. For instance, and without limitation, third prognostic output may represent a mutually exclusive alternative to a second prognostic output 712, indicating that the second prognostic output 712 is unlikely to be correct, and/or may be linked by way of generating another output from causal link learner 152 to a prognostic output matching a different prognostic label from that in a second prognostic output 712, which may be eliminated as contradictory. As a non-limiting example, an elevated urea level may be detected in second biological extraction, mapping to a third prognostic output associated with gout; gout may be selected from a plurality of second prognostic outputs 712, and/or rheumatoid arthritis eliminated from plurality of second prognostic outputs 712, as a result.

With continued reference to FIG. 1, and as another non-limiting example, classification device 104 may be configured to receive a user instruction selecting one of the plurality of second classification device 104s and select the second prognostic output 712 as a function of the user instruction. For instance, and as indicated above, multiple possible results associated with plurality of second prognostic outputs 712 may be displayed, conveyed to a user output device 160, or the like; a medical professional may, of instance, select a second prognostic output 712 of a plurality of prognostic outputs using his or her medical judgement, combined with patient history, test results, or the like. Processes for selection may, as a further non-limiting example, include presenting multiple possible results to a medical practitioner, informing the medical practitioner that one or more follow-up tests and/or biological extractions are needed to further determine a more definite prognostic label; such follow-up tests may be used to obtain at least a second biological extraction to be used as described above.

Still referring to FIG. 1, system 100 and/or classification device 104 may be configured to determine that the at least a second prognostic output 712 includes a fundamental prognostic label. A "fundamental prognostic label," as used herein, is. Determination may include identifying, in a listing and/or data structure of fundamental prognostic labels, the at least a second prognostic output 712, and/or a second prognostic output 712 of the at least a second prognostic output 712. In an embodiment, classification device 104 may query a fundamental label listing 164, which may list prognostic labels and indications of whether prognostic labels are fundamental prognostic labels; fundamental label listing 164 may, as a non-limiting example, contain only fundamental prognostic labels. Classification device 104 may use expert fundamental listing 424 to populate fundamental label listing 164. For instance, and without limitation, classification device 104 may perform a statistical process, such as without limitation any process described above as usable for machine-learning and/or language processing, to identify fundamental prognostic labels based on entries in expert fundamental listing; statistical processes may include, without limitation, enumeration of entries in the expert fundamental listing 424 indicating that a given prognostic label is fundamental and comparison of such enumerations to threshold numbers. Alternatively or additionally, classification device may determine whether a given prognostic label is a fundamental prognostic label by directly querying expert fundamental listing 424.

Alternatively or additionally, and still referring to FIG. 1, classification device 104 may be configured to receive a user indication that at least a second prognostic output 712 and/or a second prognostic output 712 of the at least a second prognostic output 712 represents a fundamental prognostic label. A medical professional may, as a non-limiting example, identify at least a second prognostic output 712 as a fundamental cause of a condition identified in at least a first prognostic output and enter a user instruction indicating the at least a second prognostic output 712 is a fundamental cause of the first prognostic output and/or the condition indicated thereby. A medical professional may, as a non-limiting example, identify at least a second prognostic output 712 as not being a fundamental cause of a condition identified in at least a first prognostic output and enter a user instruction indicating the at least a second prognostic output 712 is not a fundamental cause of the first prognostic output and/or the condition indicated thereby, and/or may enter an instruction to repeat one or more steps described above, such as an instruction that causes causal link learner 152 to generate at least a third or subsequent prognostic output that indicates a cause of at least a second prognostic output 712; any step described in this disclosure may then be used to determine whether the at least a third or subsequent prognostic output identifies and/or includes a fundamental prognostic label, with additional repetitions of the above process being performed until discovery of a fundamental prognostic label and/or user instruction to cease iteration. Iterative use of causal link learner 152 to find at least a prognostic output identifying a cause of a previously generate at least a prognostic output may be performed automatically; for instance, where a given prognostic output is not identified as fundamental in a listing and/or database as described above, classification device 104 may cause causal link learner 152 to repeatedly output causally linked prognostic labels until a fundamental prognostic label is generated, and/or until causal link learner 152 cannot generate further causally linked prognostic labels and/or outputs.

Embodiments of system 100 may furnish augmented intelligence systems that facilitate diagnostic, prognostic, curative, and/or therapeutic decisions by medical professionals such as doctors. System 100 may provide fully automated tools and resources for each doctor to handle, process, diagnosis, develop treatment plans, facilitate and monitor all patient implementation, and record each patient status. Provision of expert system elements via expert inputs and document-driven language analysis may ensure that recommendations generated by system 100 are backed by the very best medical knowledge and practices in the world. Models and/or learners with access to data in depth may enable generation of recommendations that are directly personalized for each patient, providing complete confidence, mitigated risk, and complete transparency. Access to well-organized and personalized knowledge in depth may greatly enhance efficiency of medical visits; in embodiments, a comprehensive visit may be completed in as little as 10 minutes. Recommendations may further suggest follow up testing and/or therapy, ensuring an effective ongoing treatment and prognostic plan.

Figure 8:
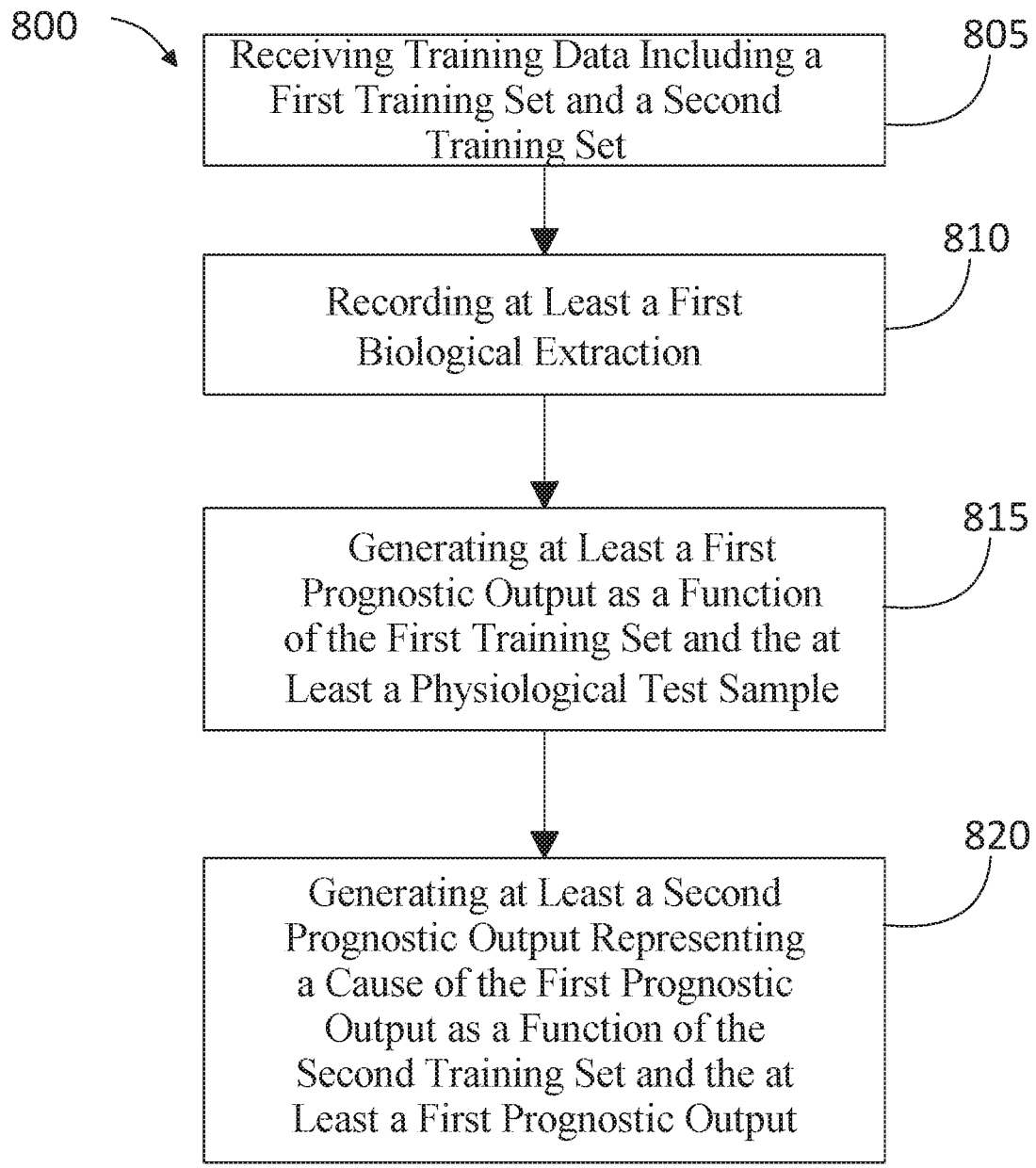
FIG. 8 illustrates flow diagram illustrating an exemplary embodiment of a method of causative chaining of prognostic label classifications.

Turning now to FIG. 8, an exemplary embodiment of a method 800 of causative chaining of prognostic label classifications is illustrated. At step 805, a classification device 104 receives training data. Training data may include any training data as described above in reference to 1-7. Receiving training data may include receiving a first training set 108 including a plurality of first data entries, each first data entry of the plurality of first data entries including at least a first element of physiological state data and at least a correlated first prognostic label 116; this may be implemented, without limitation, as described above in reference to FIGS. 1-7. Receiving training data may include receiving a second training set 128 including a plurality of second data entries, each second data entry of the plurality of second data entries including at least a second prognostic label 132 and at least a correlated third prognostic label; this may be implemented as described above in reference to FIGS. 1-7. Second training set 128 may include at least a data entry including at least a second element of physiological state data 140 and at least a correlated fourth prognostic label, for instance and without limitation as described above in reference to FIGS. 1-7. At step 810, classification device 104 records at least a first biological extraction.

Still referring to FIG. 8, at step 815, classification device 104 generates at least a first prognostic output as a function of the first training set 108 and the at least a physiological test sample. This may be implemented as described above in reference to FIGS. 1-7. At step 820, classification device 104 generates at least a second prognostic output 712 as a function of the second training set 128 and the at least a first prognostic output, where the at least a second prognostic output 712 represents a cause of the at least a first prognostic output; this may be implemented as described above in reference to FIGS. 1-7. Classification device 104 may generate second prognostic output 712 by generating the second prognostic output 712 as a function of the second training set 128, the first prognostic output, and the at least a biological extraction. For instance, classification device 104 and/or causal link learner 152 may generate a model relating a mathematical function of physiological state data and prognostic labels to prognostic labels, and/or may detect such a relationship using a lazy learning algorithm as described above in reference to FIGS. 1-7. In such an embodiment, this may permit classification device 104 and/or causal link learner 152 to select at least a second prognostic output 712 that represents a potential cause of at least a first prognostic output and is consistent with at least a first biological extraction; classification device 104 and/or causal link learner 152 may alternatively or additionally regenerate at least a second prognostic output 712 as a function of the first prognostic output, the second training set 128, and at least a second biological extraction, and/or as a function of the first prognostic output, the second training set 128, the at least a second biological extraction and the at least a first biological extraction, to select a second biological extraction from a plurality of second biological extractions as described above.

Still referring to FIG. 8, in an embodiment, where at least a second prognostic output 712 further comprises a plurality of second prognostic outputs 712, classification device 104 may select a second prognostic output 712 from the plurality of second prognostic outputs 712; this may be implemented according to any process or process step described above. For instance, and without limitation, selecting the second prognostic output 712 may include receiving at least a second biological extraction and selecting the second prognostic output 712 from the plurality of second prognostic outputs 712 as a function of the at least a second biological extraction, which may be performed according to any process or process steps as described in this disclosure. Selecting second prognostic output 712 from the plurality of prognostic outputs based on the at least a second biological extraction may include generating a third prognostic output as a function of the first training set 108 and the at least a second biological extraction and selecting second prognostic output 712 from the plurality of second prognostic outputs 712 as a function of the third prognostic output, for instance as described above in reference to FIGS. 1-7. Selecting a second prognostic output 712 from the plurality of second prognostic outputs 712 may include selecting the second prognostic output 712 by determining that the second prognostic output 712 matches third prognostic output, for instance as described above in reference to FIGS. 1-7. Selecting a second prognostic output 712 from the plurality of second prognostic outputs 712 may include determining that a prognostic output of the plurality of second prognostic outputs 712 contradicts third prognostic output, for instance as described above in reference to FIGS. 1-7. Selecting the second prognostic output 712 from the plurality of second prognostic outputs 712 may include receiving a user instruction selecting one of the plurality of second classification device 104s and selecting the second prognostic output 712 as a function of the user instruction; this may be implemented as described above in reference to FIGS. 1-7.

In an embodiment, and still referring to FIG. 8, classification device 104 may determine that the at least a second prognostic output 712 includes a fundamental prognostic label. This determination may be performed according to any process or process steps described above in reference to FIG. 1-7. Any step or steps of method 800 may be repeated, in any order. As a non-limiting example, steps of method 800 may be performed iteratively to find one or more fundamental prognostic labels associated with at least a first prognostic label 116, for instance as described elsewhere in this disclosure.

Figure 9:
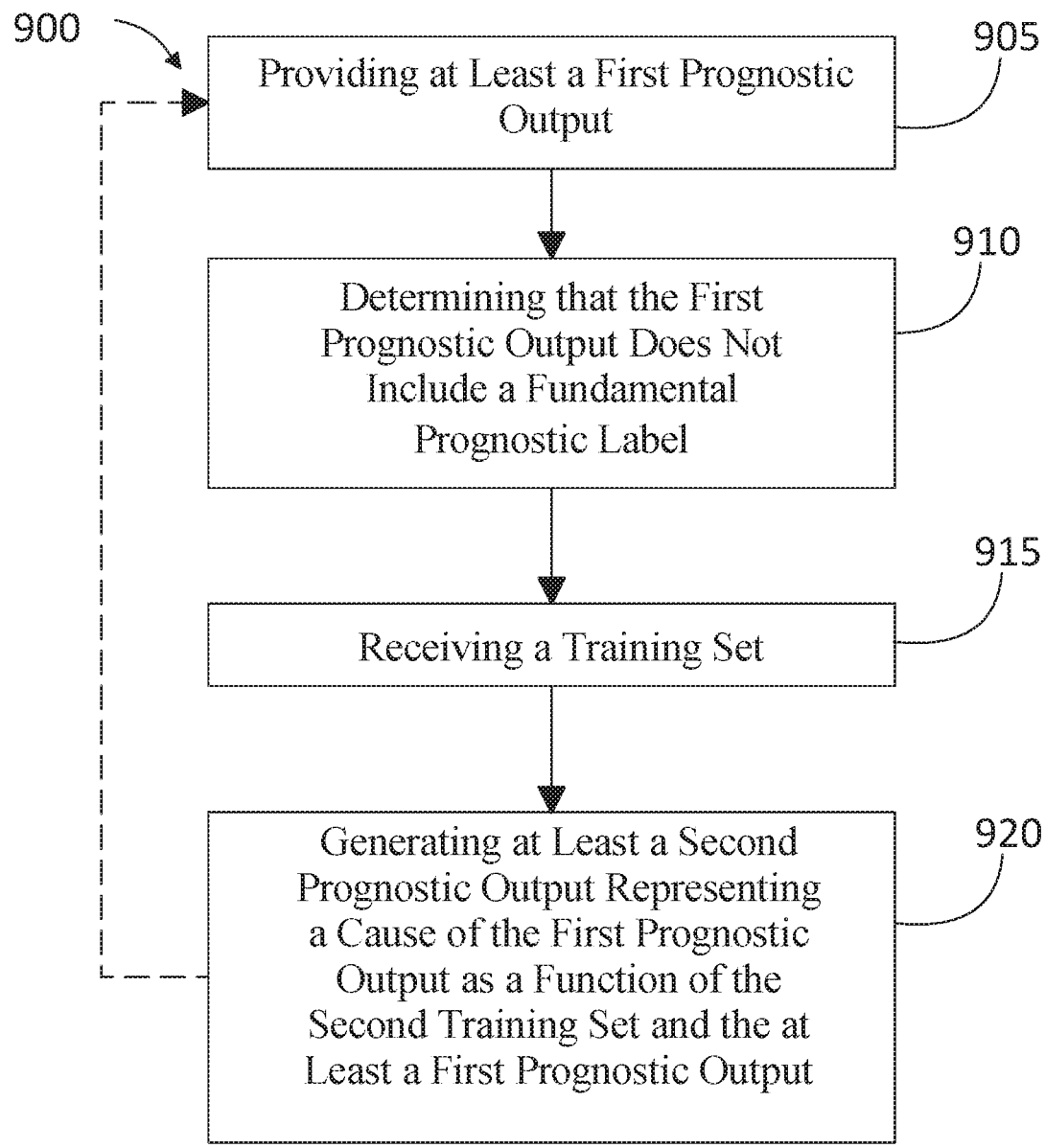
FIG. 9 illustrates flow diagram illustrating an exemplary embodiment of a method of causative chaining of prognostic label classifications.

Turning now to FIG. 9, an exemplary embodiment of a method 900 of causative chaining of prognostic label classifications is illustrated. At step 905, at least a first prognostic output is provided at a classification device 104. At least a first prognostic output may be generated using any process described in this disclosure for generation of a prognostic output, including any step or steps of method 800. At least a first prognostic output may have been generated by a previous iteration of an embodiment of method 900; in other words, at least a first prognostic output may include and/or be at least a second prognostic output produced in a previous iteration of an embodiment of method 900.

At step 910, and still referring to FIG. 9, classification device 104 determines that first prognostic output does not include a fundamental prognostic label; classification device 104 may make this determination, using any component, components, and/or steps described above in reference to FIGS. 1-8. For instance, and without limitation, classification device 104 may determine that first prognostic output does not include a fundamental prognostic label by querying fundamental label listing 164 and/or expert fundamental listing 424; alternatively or additionally, a user such as a medical professional may enter an instruction indicating that the at least a first prognostic output does not include a fundamental prognostic label.

At step 915, and with continued reference to FIG. 9, classification device receives a training set including a plurality of data entries, each data entry of the plurality of data entries including at least a first prognostic label 116 and at least a correlated second prognostic label 132; this may be accomplished as described above, in reference to FIGS. 1-8, for reception of second training set 128.

At step 920, and still referring to FIG. 9, classification device 104 generates at least a second prognostic output as a function of the training set and the at least a first prognostic output, wherein the at least a second prognostic output represents a cause of the at least a first prognostic output; this may be performed as described above in reference to FIGS. 1-8, for instance and without limitation as described for generation of at least a second prognostic output 712.

In an embodiment, and still referring to FIG. 9, one or more method steps in this disclosure, including without limitation one or more steps of embodiments of method 900, may be repeated or performed iteratively. For instance, and without limitation, method 900 as described above may be repeatedly performed, with each iteration using a prognostic output of the at least a second prognostic output of the previous iteration as the at least a first prognostic output for the current iteration, until a termination condition occurs. Termination condition may include identification of a second prognostic output as containing a fundamental prognostic label, where identification may be performed according to any process for determining that a prognostic label is a fundamental prognostic label as described above. Termination condition may include entry of a user command to terminate. In lieu of detection that first prognostic output does not include a fundamental prognostic label, an alternative embodiment of method 900 may include receiving a user command to generate second prognostic output; a user, such as a medical professional, may reenter such commands until satisfied with the number of iterations and/or the second prognostic output generated.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
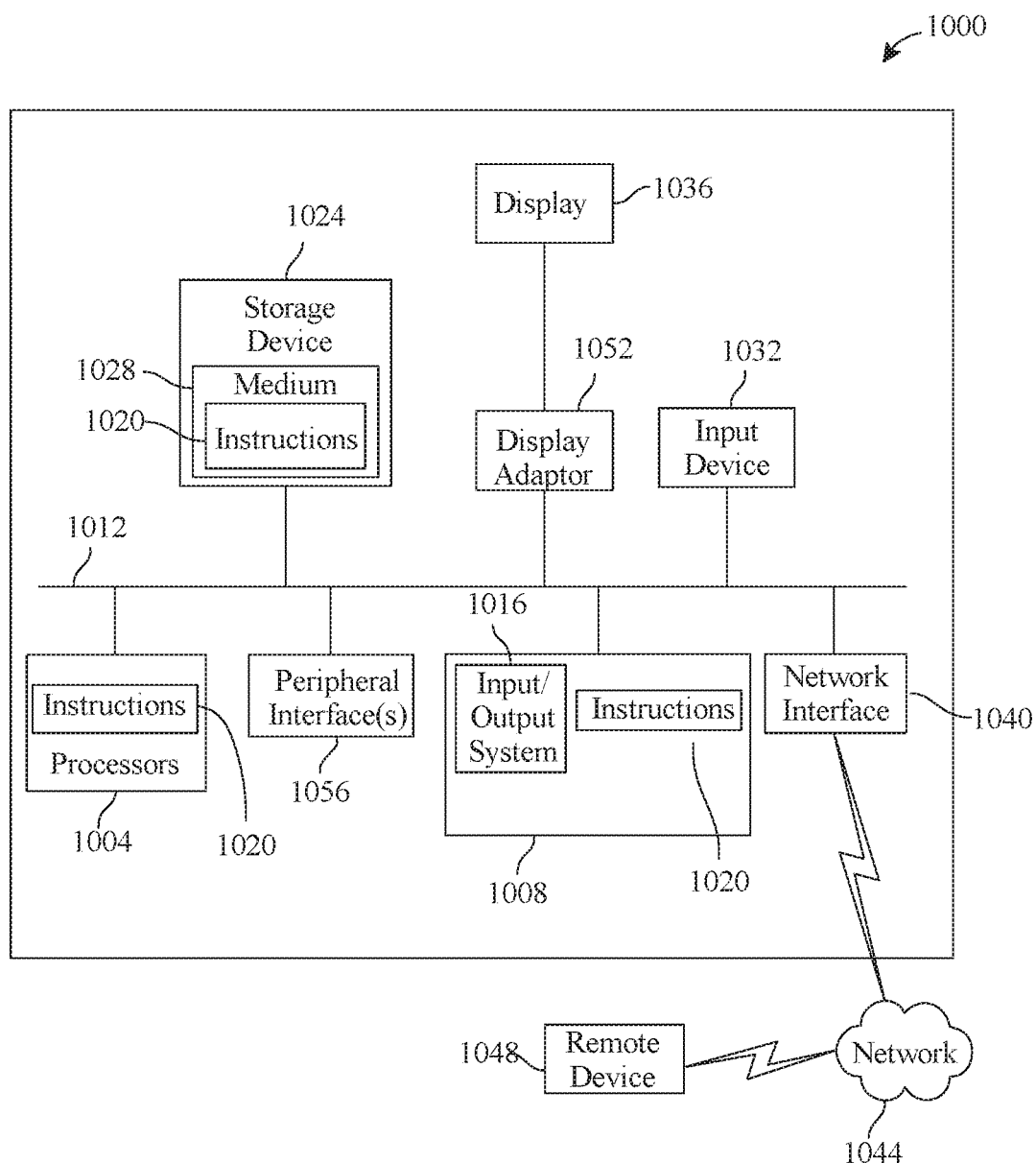
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Memory 1008 may include various components (e.g., machine-readable media) including, but not limited to, a random access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alpha-numeric input device (e.g., a keyboard), a pointing device, ajoystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIREWIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for causative chaining of prognostic label classifications, the system comprising:
 at least a computing device, the computing device designed and configured to:
 receive training data, wherein receiving the training data further comprises:
 receiving a first training set including a plurality of first data entries, each first data entry of the plurality of first data entries including at least a first element of physiological state data and at least a correlated first prognostic label; and receiving a second training set including a plurality of second data entries, each second data entry of the plurality of second data entries including at least a second prognostic label and at least a correlated third prognostic label;

record at least a first biological extraction;

display one or more follow-up suggestions for acquisition of at least a second biological extraction at a user output device; and receive the at least a second biological extraction;

a prognostic label learner operating on the at least a computing device, the prognostic label learner designed and configured to generate at least a first prognostic output as a function of the first training set and the at least a physiological test sample, wherein the prognostic label learner is further configured to generate a third prognostic output as a function of the first training set and the at least a second biological extraction; and a causal link learner operating on the at least a computing device, the causal link learner designed and configured to generate at least a second prognostic output as a function of the second training set and the at least a first prognostic output, wherein the at least a second prognostic output represents a cause of the at least a first prognostic output, and wherein the at least a second prognostic output further comprises a plurality of second prognostic outputs;

wherein the at least a computing device is further configured to:
determine that a single prognostic output of the plurality of second prognostic outputs contradicts the third prognostic output; and
eliminate the single prognostic output from the plurality of second prognostic outputs.

2. The system of claim 1, wherein the second training set further comprises at least a data entry including at least a second element of physiological data and at least a correlated fourth prognostic label.

3. The system of claim 2, wherein the causal link learner is further configured to generate the second prognostic output as a function of the second training set, the first prognostic output, and the at least a biological extraction.

4. The system of claim 1, wherein the at least a computing device is configured to select a second prognostic output from the plurality of second prognostic outputs by determining that the second prognostic output matches the third prognostic output.

5. The system of claim 1, wherein the at least a computing device is further configured to determine that the at least a second prognostic output includes a fundamental prognostic label by querying a fundamental label listing, the fundamental label listing containing a plurality of entries, each of the entries indicating a fourth prognostic label that at least an expert has identified as a root cause of a condition associated with at least a fifth prognostic label.

6. A method of causative chaining of prognostic label classifications, the method comprising:
receiving, by at least a computing device, training data, wherein receiving the training data further comprises:
receiving a first training set including a plurality of first data entries, each first data entry of the plurality of first data entries including at least a first element of physiological state data and at least a correlated first prognostic label; and receiving a second training set including a plurality of second data entries, each second data entry of the plurality of second data entries including at least a second prognostic label and at least a correlated third prognostic label; and recording, by the at least a computing device, at least a first biological extraction;

displaying one or more follow-up suggestions for acquisition of at least a second biological extraction at a user output device; and receiving the at least a second biological extraction;

generating, by the computing device, at least a first prognostic output as a function of the first training set and the at least a physiological test sample;

generating, by the at least a computing device, a third prognostic output as a function of the first training set and the at least a second biological extraction;

generating, by the at least a computing device, at least a second prognostic output as a function of the second training set and the at least a first prognostic output, wherein the at least a second prognostic output represents a cause of the at least a first prognostic output, the at least a second prognostic output further comprising a plurality of second prognostic outputs;

determining that a single prognostic output of the plurality of second prognostic outputs contradicts the third prognostic output; and eliminating the single prognostic output from the plurality of second prognostic outputs.

7. The method of claim 6, wherein the second training set further comprises at least a data entry including at least a second element of physiological data and at least a correlated fourth prognostic label.

8. The method of claim 7, wherein generating the second prognostic output further comprises generating the second prognostic output as a function of the second training set, the first prognostic output, and the at least a biological extraction.

9. The method of claim 6, further comprising selecting a second prognostic output from the plurality of second prognostic outputs by determining that the second prognostic output matches the third prognostic output.

10. The method of claim 6, further comprising determining that the at least a second prognostic output includes a fundamental prognostic label by querying a fundamental label listing, the fundamental label listing containing a plurality of entries, each of the entries indicating a fourth prognostic label that at least an expert has identified as a root cause of a condition associated with at least a fifth prognostic label.

11. The system of claim 1, wherein the causal link learner is configured to generate the at least a second prognostic output by executing a K-nearest neighbors algorithm as a function of the second training set and the at least a first prognostic output.

12. The method of claim 6, further comprising generating the at least a second prognostic output by executing a K-nearest neighbors algorithm as a function of the second training set and the at least a first prognostic output.

* * * * *